(12) United States Patent
Chen et al.

(10) Patent No.: US 11,458,220 B2
(45) Date of Patent: Oct. 4, 2022

(54) MICROBIAL DISINFECTION FOR PERSONAL PROTECTION EQUIPMENT

(71) Applicant: Singletto Inc., Seattle, WA (US)

(72) Inventors: James Chongchu Chen, Clyde Hill, WA (US); Celesta Jane Bjornson, Seattle, WA (US); John David Bjornson, Seattle, WA (US); LuAnn Lawton Chen, Clyde Hill, WA (US); Stephanie Marie Chong-Ming Chen, Makawao, HI (US); Daniel Duong Hoang, Seattle, WA (US); Kathleen Clare Lendvay, Seattle, WA (US); Paul Deven Rolley, Chicago, IL (US)

(73) Assignee: Singletto Inc., Seattle, WA (US)

( * ) Notice: Subject to any disclaimer, the term of this patent is extended or adjusted under 35 U.S.C. 154(b) by 0 days.

(21) Appl. No.: 17/522,811

(22) Filed: Nov. 9, 2021

(65) Prior Publication Data

US 2022/0143243 A1    May 12, 2022

Related U.S. Application Data

(60) Provisional application No. 63/192,980, filed on May 25, 2021, provisional application No. 63/113,060, filed on Nov. 12, 2020.

(51) Int. Cl.
*A61L 2/18* (2006.01)
*A61L 2/20* (2006.01)

(52) U.S. Cl.
CPC .................. *A61L 2/18* (2013.01); *A61L 2/20* (2013.01); *A61L 2202/11* (2013.01); *A61L 2202/15* (2013.01); *A61L 2202/16* (2013.01)

(58) Field of Classification Search
CPC .......... A61L 2/18; A61L 2/20; A61L 2202/11; A61L 2202/15; A61L 2202/16
See application file for complete search history.

(56) References Cited

U.S. PATENT DOCUMENTS

| 2,547,825 A | 4/1951 | King |
| 2,637,887 A | 5/1953 | Goodman et al. |

(Continued)

FOREIGN PATENT DOCUMENTS

| AU | 2006341380 B2 | 1/2013 |
| AU | 2013202001 A1 | 4/2013 |

(Continued)

OTHER PUBLICATIONS

Kim, Michele M. et al., "Light Sources and Dosimetry Techniques for Photodynamic Therapy," Photochemistry and Photobiology, 2020, vol. 96, pp. 280-294.

(Continued)

*Primary Examiner* — Regina M Yoo
(74) *Attorney, Agent, or Firm* — John W. Branch; Branch Partners PLLC

(57) ABSTRACT

A photosensitizer formulation can be disposed on or in a mesh; net; netting; screen; curtain of strands, fibers, or monofilaments; substrate, personal protective gear, mask, or any other suitable object. The photosensitizer formulation, when in contact with molecular oxygen and activated by light or ultrasound, produces microbicidal singlet oxygen. A variety of different arrangements and applications are described. For example, an air flow device may also be included to generate a flow of air through or over the photosensitizer formulation. A fluorescent formulation may be included to monitor photobleaching. The photosensitizer formulation may be disposed in a concentration gradient to generate antigenic particles by damaging or destroying microbes.

6 Claims, 20 Drawing Sheets

(56) References Cited

U.S. PATENT DOCUMENTS

| | | | |
|---|---|---|---|
| 3,674,486 A * | 7/1972 | Milgrom | G03F 7/038 |
| | | | 430/286.1 |
| 3,817,389 A | 6/1974 | Weichselbaum | |
| 4,382,079 A | 5/1983 | Marschner | |
| 4,395,789 A | 8/1983 | Bruce | |
| 4,402,318 A | 9/1983 | Swartz | |
| 4,775,348 A | 10/1988 | Collins | |
| 5,344,051 A | 9/1994 | Brown | |
| 5,366,402 A | 11/1994 | Rudell et al. | |
| 5,445,608 A | 8/1995 | Chen et al. | |
| 5,526,957 A | 6/1996 | Brown et al. | |
| 5,569,477 A | 10/1996 | Nesbitt | |
| 5,715,837 A | 2/1998 | Chen | |
| 5,741,316 A | 4/1998 | Chen et al. | |
| 5,766,234 A | 6/1998 | Chen et al. | |
| 5,782,896 A | 7/1998 | Chen et al. | |
| 5,814,008 A | 9/1998 | Chen et al. | |
| 5,827,186 A | 10/1998 | Chen et al. | |
| 5,830,526 A | 11/1998 | Wilson et al. | |
| 5,865,840 A | 2/1999 | Chen | |
| 5,997,569 A | 12/1999 | Chen et al. | |
| 6,004,510 A * | 12/1999 | Gilbert | A01N 59/16 |
| | | | 514/840 |
| 6,080,160 A | 6/2000 | Chen et al. | |
| 6,096,066 A | 8/2000 | Chen et al. | |
| 6,210,425 B1 | 4/2001 | Chen | |
| 6,238,426 B1 | 5/2001 | Chen | |
| 6,273,904 B1 | 8/2001 | Chen et al. | |
| 6,281,611 B1 | 8/2001 | Chen et al. | |
| 6,319,273 B1 | 11/2001 | Chen et al. | |
| 6,331,744 B1 | 12/2001 | Chen et al. | |
| 6,344,050 B1 | 2/2002 | Chen | |
| 6,416,531 B2 | 7/2002 | Chen | |
| 6,420,455 B1 | 7/2002 | Landgrebe et al. | |
| 6,443,978 B1 * | 9/2002 | Zharov | A61N 5/0616 |
| | | | 606/2 |
| 6,454,789 B1 | 9/2002 | Chen et al. | |
| 6,520,669 B1 | 2/2003 | Chen et al. | |
| 6,572,839 B2 | 6/2003 | Sugita et al. | |
| 6,580,228 B1 | 6/2003 | Chen et al. | |
| 6,606,767 B2 | 8/2003 | Wong | |
| 6,635,267 B1 | 10/2003 | Miyoshi et al. | |
| 6,691,898 B2 | 2/2004 | Hurray et al. | |
| 6,846,305 B2 | 1/2005 | Smith et al. | |
| 6,860,782 B2 | 3/2005 | Hornsby et al. | |
| 7,018,395 B2 | 3/2006 | Chen | |
| 7,087,219 B2 | 8/2006 | Burzynski et al. | |
| 7,288,106 B2 | 10/2007 | Heacock et al. | |
| 7,320,158 B2 | 1/2008 | Deto et al. | |
| 7,320,786 B2 | 1/2008 | Chen | |
| 7,511,031 B2 | 3/2009 | Chen | |
| 7,611,033 B2 | 11/2009 | Ganzeboom | |
| 7,802,572 B2 | 9/2010 | Hahne | |
| RE42,610 E | 8/2011 | Schramm | |
| 8,057,464 B2 | 11/2011 | Chen et al. | |
| 8,226,946 B2 | 7/2012 | Chen | |
| 8,283,135 B2 | 10/2012 | Doyle et al. | |
| 8,293,802 B2 | 10/2012 | Modak et al. | |
| 8,439,674 B2 | 5/2013 | Li et al. | |
| 8,450,359 B2 | 5/2013 | McCoy et al. | |
| 8,484,809 B2 | 7/2013 | Fiedler | |
| 8,545,120 B2 | 10/2013 | Breidenbach et al. | |
| 8,616,414 B2 | 12/2013 | Ciavarella | |
| 8,685,005 B2 | 4/2014 | Dahm et al. | |
| 8,685,067 B2 | 4/2014 | Burwell et al. | |
| 8,759,092 B2 | 6/2014 | Goodrich | |
| 9,073,066 B2 | 7/2015 | Banks et al. | |
| 9,080,976 B2 | 7/2015 | Hackbarth et al. | |
| 9,114,971 B2 | 8/2015 | Rasmussen et al. | |
| 9,140,030 B2 | 9/2015 | Jin | |
| 9,149,651 B2 | 10/2015 | Keltner et al. | |
| 9,167,880 B2 | 10/2015 | Wilson et al. | |
| 9,278,148 B2 | 3/2016 | Fewkes et al. | |
| 9,352,074 B2 | 5/2016 | Gros | |
| 9,480,760 B2 * | 11/2016 | Appeaning | A61L 2/088 |
| 9,527,918 B2 | 12/2016 | Fiori et al. | |
| 10,105,386 B2 | 10/2018 | Vehige et al. | |
| 10,175,687 B2 | 1/2019 | Lema et al. | |
| 10,307,610 B2 | 6/2019 | Keltner et al. | |
| 10,327,444 B2 | 6/2019 | Topchik | |
| 10,666,928 B2 | 5/2020 | Liu | |
| 2002/0088825 A1 | 7/2002 | Laverdure | |
| 2003/0114434 A1 | 6/2003 | Chen et al. | |
| 2006/0223729 A1 | 10/2006 | Hamblin et al. | |
| 2007/0038204 A1 | 2/2007 | Chen et al. | |
| 2007/0059316 A1 | 3/2007 | Pallenberg et al. | |
| 2007/0059791 A1 | 3/2007 | Goodrich | |
| 2007/0129776 A1 | 6/2007 | Robins et al. | |
| 2007/0133935 A1 | 6/2007 | Fine | |
| 2007/0142880 A1 | 6/2007 | Barnard et al. | |
| 2007/0286878 A1 | 12/2007 | Harruna | |
| 2008/0015189 A1 | 1/2008 | Hamblin et al. | |
| 2008/0107636 A1 | 5/2008 | Goodrich et al. | |
| 2009/0317293 A1 | 12/2009 | Street et al. | |
| 2009/0317436 A1 | 12/2009 | Wilson et al. | |
| 2010/0241054 A1 | 9/2010 | Dacey, Jr. et al. | |
| 2010/0261798 A1 | 10/2010 | Neuss et al. | |
| 2010/0274330 A1 | 10/2010 | Burwell et al. | |
| 2010/0305436 A1 | 12/2010 | Chen et al. | |
| 2011/0008372 A1 | 1/2011 | Chen | |
| 2011/0009464 A1 | 1/2011 | Chen | |
| 2011/0014239 A1 | 1/2011 | Goodrich | |
| 2011/0110818 A1 | 5/2011 | Mowbray-d'Arbela et al. | |
| 2011/0152219 A1 | 6/2011 | Stagni et al. | |
| 2012/0100039 A1 * | 4/2012 | Appeaning | A61L 2/088 |
| | | | 422/186.01 |
| 2012/0209359 A1 | 8/2012 | Chen et al. | |
| 2013/0251440 A1 | 9/2013 | Young et al. | |
| 2013/0289457 A1 | 10/2013 | Young et al. | |
| 2014/0052050 A1 | 2/2014 | Courtin | |
| 2014/0303547 A1 | 10/2014 | Loupis et al. | |
| 2016/0091399 A1 | 3/2016 | Chen et al. | |
| 2016/0193338 A1 | 7/2016 | Loupis et al. | |
| 2016/0220728 A1 | 8/2016 | Adams et al. | |
| 2016/0270895 A1 | 9/2016 | Zoll et al. | |
| 2016/0310758 A1 | 10/2016 | Friedman et al. | |
| 2017/0056603 A1 | 3/2017 | Cowan et al. | |
| 2018/0099063 A1 | 4/2018 | Lyons et al. | |
| 2018/0160720 A1 | 6/2018 | Von Hasseln | |
| 2018/0214552 A1 * | 8/2018 | Sui | A61K 47/6957 |
| 2018/0243790 A1 | 8/2018 | Grossman et al. | |
| 2019/0161562 A1 | 5/2019 | Bakar et al. | |
| 2019/0209857 A1 | 7/2019 | Brawn et al. | |
| 2019/0314502 A1 | 10/2019 | Wei et al. | |
| 2020/0315280 A1 | 10/2020 | Kaye | |
| 2022/0054149 A1 | 2/2022 | Chen et al. | |
| 2022/0054667 A1 | 2/2022 | Chen et al. | |
| 2022/0054672 A1 * | 2/2022 | Chen | A61L 2/088 |
| 2022/0061318 A1 | 3/2022 | Chen et al. | |
| 2022/0062461 A1 | 3/2022 | Chen et al. | |

FOREIGN PATENT DOCUMENTS

| | | |
|---|---|---|
| AU | 2015200474 B2 | 2/2015 |
| AU | 2016235771 B2 | 9/2016 |
| AU | 2016235788 A1 | 9/2016 |
| CA | 2276023 C | 4/2002 |
| CA | 2428099 C | 6/2002 |
| CA | 2473924 A1 | 7/2003 |
| CA | 2537235 A1 | 1/2005 |
| CA | 2693491 C | 10/2014 |
| CN | 102115951 B | 7/2012 |
| CN | 101479438 B | 5/2014 |
| CN | 104138310 A | 11/2014 |
| CN | 205094776 U | 3/2016 |
| CN | 104589717 B | 3/2017 |
| CN | 208597758 U | 3/2019 |
| CN | 107353723 B | 5/2020 |
| EP | 1644082 A2 | 4/2006 |
| EP | 1684865 A1 | 8/2006 |
| EP | 2181691 A1 | 5/2010 |
| EP | 1429993 B1 | 1/2011 |
| EP | 1940907 B1 | 4/2011 |
| EP | 2428461 B1 | 4/2013 |

(56) References Cited

FOREIGN PATENT DOCUMENTS

| | | |
|---|---|---|
| GB | 2374856 A | 10/2002 |
| GB | 2482745 A | 2/2012 |
| JP | 2004-275927 A | 10/2004 |
| JP | 2005-009065 A | 1/2005 |
| JP | 2005506938 A | 3/2005 |
| JP | 2005-112791 A | 4/2005 |
| JP | 4238174 B2 | 3/2009 |
| JP | 4536377 B2 | 9/2010 |
| JP | 2014-004329 A | 1/2014 |
| JP | 5632478 B2 | 11/2014 |
| JP | 2015-159819 A | 9/2015 |
| KR | 200348162 Y1 | 5/2004 |
| KR | 100822777 B1 | 4/2008 |
| KR | 2014028671 A * | 3/2014 ............... A61N 5/06 |
| KR | 20170076342 A | 7/2017 |
| KR | 20170082259 A | 7/2017 |
| PL | 230175 B1 | 9/2018 |
| RU | 2397127 C2 | 8/2010 |
| TW | I610806 B | 1/2018 |
| WO | 98/32494 A1 | 7/1998 |
| WO | 1999018924 A1 | 4/1999 |
| WO | 99/49823 A1 | 10/1999 |
| WO | 2000004930 A2 | 2/2000 |
| WO | 2004108249 A1 | 12/2004 |
| WO | 2005032459 A2 | 4/2005 |
| WO | 2006086770 A2 | 8/2006 |
| WO | 2007103781 A2 | 9/2007 |
| WO | 2008046019 A1 | 4/2008 |
| WO | 2009132223 A | 10/2009 |
| WO | 2010076658 A2 | 7/2010 |
| WO | 2014130740 A1 | 8/2014 |
| WO | 2016039812 A1 | 3/2016 |
| WO | 2018022926 A1 | 2/2018 |
| WO | 2018151236 A1 | 8/2018 |
| WO | 2019183320 A1 | 9/2019 |
| WO | 2021001441 A1 | 1/2021 |
| WO | 2021001445 A1 | 1/2021 |

OTHER PUBLICATIONS

Menichini, Federica et al., "In vitro photo-induced cytotoxic activity of Citrus bergamia and C. medica L. cv. Diamante peel essential oils and identified active coumarins," Pharmaceutical Biology, vol. 48, No. 9, pp. 1059-1065.
Yu, Jing et al., "Green preparation of carbon dots by Jinhua bergamot for sensitive and selective fluorescent detection of Hg2+ and Fe3+," Sensors and Actuators B: Chemical, 2015, vol. 214, pp. 29-35.
Akasov, Roman A. et al., "Photodynamic therapy of melanoma by blue-light photoactivation of flavin mononucleotide," Scientific Reports, 2019, vol. 9, Article No. 9679, pp. 1-11.
Sigma-Aldrich, "Hyaluronic acid sodium salt," https://www.sigmaaldrich.com/US/en/product/sigma/h5542, Accessed: Nov. 22, 2021, pp. 1-5.
Alven, Sibusiso et al., "Hyaluronic Acid-Based Scaffolds as Potential Bioactive Wound Dressings," Polymers, 2021, vol. 13, No. 2102, pp. 1-20.
RadiologyInfo, "Intravascular Ultrasound," https://www.radiologyinfo.org/en/info/ultrasound-intravascular, Accessed: Nov. 22, 2021, pp. 1-6.
Malewar, Amit, "Tengujo, the world's thinnest paper, almost completely transparent," Inceptive Mind, https://www.inceptivemind.com/tengujo-worlds-thinnest-paper-nearly-transparent/13273/, Accessed: Nov. 15, 2021, pp. 1-5.
Nakonechny, Faina et al., "Aspects of Photodynamic Inactivation of Bacteria," Microorganisms, 2020, Chapter 7, pp. 131-151.
Mesquita, Mariana Q. et al., "Revisiting Current Photoactive Materials for Antimicrobial Photodynamic Therapy," Molecules, 2018, vol. 23, No. 2424, pp. 1-47.
Seghatchian, Jerard et al., "Main Properties of the Theraflex MB-Plasma System for Pathogen Reduction," Transfusion Medicine and Hemotherapy, 2011, vol. 38, No. 1, pp. 55-64.
Eickmann, Markus et al., "Inactivation of Ebola virus and Middle East respiratory syndrome coronavirus in platelet concentrates and plasma by ultraviolet C light and methylene blue plus visible light, respectively," Transfusion, 2018, vol. 58, pp. 2202-2207.
Shang, Ke et al., "Accelerated In Vitro Degradation of Optically Clear Low β-Sheet Silk Films by Enzyme-Mediated Pretreatment," Translational Vision Science & Technology, vol. 2, No. 3, Article 2, pp. 1-11.
Evonik, "A Broad Range of Standard, Custom and Specialized Biodegradable Polymers for Medical Applications," https://healthcare.evonik.com/en/medical-devices/biodegradable-materials/resomer-portfolio, Accessed: Nov. 22, 2021, pp. 1-3.
Hidakawashi Co., Ltd., "Japanese Paper TENGU," https://www.hidakawashi.com/paper-TENGU/index.html, Accessed: Nov. 15, 2021, pp. 1-2.
Yang, Wenjing et al., "3D Printing of Polymeric Multi-Layer Micro-Perforated Panels for Tunable Wideband Sound Absorption," Polymers, 2020, vol. 12, No. 360, pp. 1-17.
Bazaz, Sajad Razavi et al., "3D Printing of Inertial Microfluidic Devices," Scientific Reports, 2020, vol. 10, Article No. 5929, pp. 1-14.
Waheed, Sidra et al., "3D printed microfluidic devices: enablers and barriers," The Royal Society of Chemistry, Lab Chip, 2016, vol. 16, Iss. 11, pp. 1-21.
CDC—The National Institue for Occupational Safety and Health (NIOSH), https://vww.cdc.gov/niosh/index.htm, Accessed: Nov. 15, 2021, p. 1.
Shirata, Chikara et al., "Near-infrared photothermal/photodynamic therapy with indocyanine green induces apoptosis of hepatocellular carcinoma cells through oxidative stress," Scientific Reports, vol. 7, Article No. 13958, pp. 1-8.
Dias, Lucas D. et al., "COVID-19: Beyond the virus. The use of photodynamic therapy for the treatment of infections in the respiratory tract," Photodiagnosis and Photodynamic Therapy, Letter to the Editor, 2020, vol. 31, pp. 1-2.
Kim, Jaesung et al., "Photosensitized Production of Singlet Oxygen via C60 Fullerene Covalently Attached to Functionalized Silica-coated Stainless-Steel Mesh: Remote Bacterial and Viral Inactivation," Applied Catalysts B: Environmental, 2020, vol. 270, Article No. 118862, pp. 1-9.
Hasegawa, Keisuke et al., "Curved acceleration path of ultrasound-driven air flow," Journal of Applied Physics, vol. 125, Article No. 054902, pp. 1-6.
Sunday, Michael Oluwatoyin et al., "A simple, inexpensive method for gas-phase singlet oxygen generation from sensitizer-impregnated filters: Potential application to bacteria/virus inactivation and pollutant degradation," Science of the Total Environment, 2020, vol. 746, Article No. 141186, pp. 1-6.
Komaiko, Jennifer S. et ai., "Formation of Food-Grade Nanoemulsions Using Low-Energy Preparation Methods: A Review of Available Methods," Comprehensive Reviews in Food Science and Food Safety, 2016, vol. 15, pp. 331-352.
Chemistry Industry, "Emulsifiers," https://www.chemistryindustry.biz/emulsifiers.html, Accessed: Nov. 15, 2021, pp. 1-9.
Smartblend, "Cocktail foams, airs and bubbles—How to make them," https://www.smartblend.co.uk/blog/cocktaii-foams-airs-and-bubbies-and-how-to-make-them, Accessed: Dec. 6, 2021, pp. 1-16.
Kitchen Theory, "Lecithin & Culinary Foam," https://kitchen-theory.com/culinary-foam/, Accessed: Nov. 15, 2021, pp. 1-4.
Hillary, Sarah L. et al., "Use of methylene blue and near-infrared fluorescence in thyroid and parathyroid surgery," Langenbeck's Archives of Surgery, 2018, vol. 403, pp. 111-118.
Alander, Jarmo T. et al., "A Review of Indocyanine Green Fluorescent Imaging in Surgery," International Journal of Biomedical Imaging, 2012, vol. 2012, pp. 1-26.
Verma, Siddhartha et al., "Visualizing the effectiveness of face masks in obstructing respiratory jets," Physics of Fluids, 2020, vol. 32, pp. 1-7.
Instructables Living, "Bubble Machine," https://www.instructables.com/Bubble-Machine/, Accessed: Nov. 30, 2021, pp. 1-6.
Divangahi, Maziar et al., "Trained immunity, tolerance, priming and differentiation: distinct immunological processes," Nature Immunology, 2021, vol. 22, pp. 2-6.

(56) References Cited

OTHER PUBLICATIONS

Kumar, Sandeep et al., "Sensing Molecules with Metal-Organic Framework Functionalized Graphene Transistors," Advanced Materials, 2021, vol. 33, Article No. 2103316, pp. 1-12.
Wang, Ying et al., "Choosing optimal wavelength for photodynamic therapy of port wine stains by mathematic simulation," Journal of Biomedical Optics, 2011, vol. 16, No. 9, pp. 1-9.
Ursa BioScience, "Singlet Oxygen Sensitizers," https://ursabioscience.com/technology/singlet-oxygen-sensitizer, Accessed: Mar. 2, 2021, pp. 1-6.
Naito, Kazuya et al., "Single-molecule detection of airborne singlet oxygen," Journal of the American Chemical Society, 2006, vol. 128, No. 51, pp. 16430-16431.
Zhao, Yuanyuan et al., "Singlet oxygen generation on porous superhydrophobic surfaces: effect of gas flow and sensitizer wetting on trapping efficiency," The Journal of Physical Chemistry A, 2014, vol. 118, No. 45, pp. 10364-10371.
Gao, Rui et al., "Nano-photosensitizer based on layered double hydroxide and isophthalic acid for singlet oxygenation and photodynamic therapy," Nature Communications, 2018, vol. 9, No. 1, pp. 1-10.
Felgenträger, Ariane et al., "Singlet oxygen generation in porphyrin-doped polymeric surface coating enables antimicrobial effects on *Staphylococcus aureus*," Physical Chemistry Chemical Physics: PCCP, 2014, vol. 16, No. 38, pp. 20598-20607.
Pushalkar, Smruti et al., "Superhydrophobic Photosensitizers: Airborne 1O2 Killing of an in Vitro Oral Biofilm at the Plastron Interface," ACS Applied Materials & Interfaces, 2018, vol. 10, No. 30, pp. 25819-25829.
Hwang, Jeong-Wook et al., "Study of Singlet Oxygen Dynamics on Silicon Polymer Matrix," Journal of Analytical Methods in Chemistry, 2019, vol. 2019, pp. 1-6.
Bartusik, Dorota et al., "Bacterial Inactivation by a Singlet Oxygen Bubbler: Identifying Factors Controlling the Toxicity of 1O2 Bubbles," Environmental Science & Technology, 2012, vol. 46, No. 21, pp. 12098-12104.
Aebisher, David et al., "Superhydrophobic Surfaces as a Source of Airborne Singlet Oxygen through Free Space for Photodynamic Therapy," ACS Applied Bio Materials, 2020, vol. 3, No. 4, pp. 2370-2377.
Weaver, Eric A., "Dose Effects of Recombinant Adenovirus Immunization in Rodents," Vaccines, 2019, vol. 7, No. 4:144, pp. 1-11.
Borkar, Tanhai G. et al., "Techniques Employed in Production of Traditional Vaccines Commonly Used by Military Forces: A Review," Journal of Archives in Military Medicine, 2019, vol. 7, No. 1-2, pp. 1-12.
Hankaniemi, Minna M. et al., "A comparative study of the effect of UV and formalin inactivation on the stability and immunogenicity of a Coxsackievrius B1 vaccine," Vaccine, 2019, vol. 37, Iss. 40, pp. 5962-5971.
Mills, Devin et al., "Ultraviolet germicidal irradiation of influenza-contaminated N95 filtering facepiece respirators," American Journal of Infection Control, 2018, vol. 46, Iss. 7, pp. e49-e55.
Bull, James J. et al., "Transmissible Viral Vaccines," Trends in Microbiology, 2018, vol. 26, No. 1, pp. 6-15.
Barrett, P. Noel et al., "Vero cell technology for rapid development of inactivated whole virus vaccines for emerging viral diseases," Expert Review of Vaccines, 2017, vol. 16, Iss. 9, pp. 883-894.
Klausberger, Miriam et al., "One-shot vaccination with an insect cell-derived low-dose influenza A H7 virus-like particle preparation protects mice against H7N9 challenge," Vaccine, 2014, vol. 32, Iss. 3, pp. 355-362.
Mertes, Paul M. et ai., "Methylene blue-treated plasma: An increased allergy risk?," The Journal of Allergy and Clinical Immunology, Letters to the Editor, 2012, vol. 130, Iss. 3, pp. 808-812.
Marcus, Philip I. et ai., "In Vitro Analysis of Virus Particle Subpopulations in Candidate Live-Attenuated Influenza Vaccines Distinguishes Effective from Ineffective Vaccines," Journal of Virology, 2010, vol. 84, No. 21, pp. 10974-10981.
Quan, Fu-Shi et al., "Dose sparing enabled by skin immunization with influenza virus-like particle vaccine using microneedles," Journal of Controlled Release, 2010, vol. 147, Iss. 3, pp. 326-332.
Victoria, Joseph G. et al., "Viral Nucleic Acids in Live-Attenuated Vaccines: Detection of Minority Variants and an Adventitious Virus," Journal of Virology, 2010, vol. 84, No. 12, pp. 6033-6040.
Maves, Ryan C. et al., "Immunogenicity of a Psoralen-Inactivated Dengue Virus Type 1 Vaccine Candidate in Mice," Clinical and Vaccine Immunology, 2010, vol. 17, No. 2, pp. 304-306.
Geeraedts, Felix et al., "Superior Immunogenicity of Inactivated Whole Virus H5N1 Influenza Vaccine is Primarily Controlled by Toll-like Receptor Signalling," PLoS Pathogens, 2008, vol. 4, Iss. 8, pp. 1-8.
Monath, Thomas P. et al., "A live, attenuated recombinant West Nile virus vaccine," Proceedings of the National Academy of Sciences, 2006, vol. 103, No. 17, pp. 6694-6699.
Meurice, François et al., "Immunogenicity and Safety of a Live Attenuated Varicella Vaccine (Oka/SB Bio) in Healthy Children," The Journal of Infectious Diseases, 1996, vol. 174, Supplement 3, pp. S324-S329.
Cytiva, "Influenza vaccine manufacturing," https://www.cytivalifesciences.com/en/us/solutions/bioprocessing/knowledge-center/influenza-vaccine-manufacturing/, Accessed: Jun. 30, 2021, pp. 1-10.
Müller-Breitkreutz, Konstanze et al., "Inactivation of viruses by chemically and photochemically generated singlet molecular oxygen," Journal of Photochemistry & Photobiology B: Biology, 1995, vol. 30, Iss. 1, pp. 63-70.
Fernandez, Jim M. et al., "Singlet oxygen generation by photodynamic agents," Journal of Photochemistry & Photobiology B: Biology, 1997, vol. 37, pp. 131-140.
Rajesh, S. et al., "Antimicrobial photodynamic therapy: An overview," Journal of Indian Society of Periodontology, 2011, vol. 15, Iss. 4, pp. 323-327.
Kino, Katsuhito et al., "Commentary on the Phototoxicity and Absorption of Vitamin B2 and Its Degradation Product, Lumichrome," Pharmaceutica Analytica Acta, 2015, vol. 6, Iss. 8, pp. 1-3.
Makdoumi, Karim et al., "Different photodynamic effects of blue light with and without riboflavin on methicillin-resistant *Staphylococcus aureus* (MRSA) and human keratinocytes in vitro," Lasers in Medical Science, 2019, vol. 34, No. 9, pp. 1799-1805.
Wood, Simon et al., "Erythrosine is a potential photosensitizer for the photodynamic therapy of oral plaque biofilms," Journal of Antimicrobial Chemotherapy, 2006, vol. 57, Iss. 4, pp. 680-684.
Bhat, Manohara A. et al., "Effectiveness of erythrosine-mediated photodynamic antimicrobial chemotherapy on dental plaque aerobic microorganisms: A randomized controlled trial," Journal of Indian Society of Periodontology, 2017, vol. 21, Iss. 3, pp. 210-215.
Fecht, Sara, "The First Fully 3-D Printed LEDs Are Here," https://www.popsci.com/article/technology/first-fully-3-d-printed-leds-are-here/, 2014, Accessed: Jun. 30, 2021, pp. 1-4.
University of Southampton, "New Optical Fiber 3D Printing Technique," Optik & Photonik, 2015, vol. 10, Iss. 4, p. 17.
Molitch-Hou, Michael, "First 3D Printed Fiber Optics Created by University of Sydney Researchers with Desktop 3D Printer," 3D Printing Industry, https://3dprintingindustry.com/news/first-3d-printed-fiber-optics-createdby-university-of-sydney-researchers-with-desktop-3d-printer-55047/, 2015, Accessed: Jun. 30, 2021, p. 1.
Gahleitner, Markus et al., "Sterilization effects on polypropylene: Technology and polymer type effects," TAPPI European PLACE Conference, 2003, pp. 1-7.
Ismail, Salim et al., "Efficacy of a Novel Light-Activated Antimicrobial Coating for Disinfecting Hospital Surfaces," Infection Control and Hospital Epidemiology, 2011, vol. 32, No. 11, pp. 1130-1132.
Piccirillo, C. et al., "Antimicrobial activity of methylene blue and toluidine blue O covalently bound to a modified silicone polymer surface," Journal of Materials Chemistry, 2009, vol. 19, Iss. 34, pp. 6167-6171.
Lee, Im-Soon et al., "Aerosol Particle Size Distribution and Genetic Characteristics of Aerosolized Influenza A H1N1 Virus Vaccine Particles," Aerosol and Air Quality Research, 2011, vol. 11, pp. 230-237.

(56) References Cited

OTHER PUBLICATIONS

Meyer, Michelle et al., "Aerosolized Ebola vaccine protects primates and elicits lung-resident T cell responses," The Journal of Clinical Investigation, 2015, vol. 125, No. 8, pp. 3241-3255.
Henneberry, Brittany, "How Surgical Masks are Made," Thomas Publishing Company, https://www.thomasnet.com/articles/other/how-surgical-masks-are-made/, Accessed: Jul. 1, 2021, pp. 1-6.
Omnexus: The material selection platform, "Clear Polypropylene (PP) for Transparent Polymer Applications," https://omnexus.specialchem.com/centers/clear-polypropylene/, Accessed: Jul. 1, 2021, p. 1.
Dancer, Stephanie J., "Controlling Hospital-Acquired Infection: Focus on the Role of the Environment and New Technologies for Decontamination," Clinical Microbiology Reviews, 2014, vol. 27, No. 4, pp. 665-690.
Pyrek, Kelly M., "Portable Medical Equipment: A Significant Source of Transmission," Infection Control Today, https://www.infectioncontroltoday.com/view/portable-medical-equipment-significant-source-transmission/, Accessed: Jul. 2, 2021, pp. 1-9.
Russotto, Vincenzo et al., "Bacterial contamination of inanimate surfaces and equipment in the intensive care unit," Journal of Intensive Care, 2015, vol. 3, Article 54, pp. 1-8.
Boyce, John M., "Modern technologies for improving cleaning and disinfection of environmental surfaces in hospitals," Antimicrobial Resistance and Infection Control, 2016, vol. 5, Article 10, pp. 1-10.
Messina, Gabriele et al., "Environmental Contaminants in Hospital Settings and Progress in Disinfecting Techniques," BioMed Research International, 2013, vol. 2013, pp. 1-8.
Bonetta, Silvia et al., "Photocatalytic bacterial inactivation by TiO2-coated surfaces," AMB Express, 2013, vol. 3, Article 59, pp. 1-8.
Tamstech, "Air Permeable (Breathable) Film," http://tamstech.net/airfilm/, Accessed: Jul. 2, 2021, pp. 1-6.
Siracusa, Valentina, "Food Packaging Permeability Behaviour: A Report," International Journal of Polymer Science, 2012, vol. 2012, pp. 1-11.
Lee, Young-Ho et al., "The photodynamic therapy on *Streptococcus mutans* biofilms using erythrosine and dental halogen curing unit," International Journal of Oral Science, 2012, vol. 4, pp. 196-201.
MacoPharma, "Theraflex-MB Plasma," https://www.mhlw.go.jp/shingi/2008/05/dl/s0523-7j.pdf, Accessed: Dec. 1, 2021, pp. 1-33.
Spagnul, Cinzia et al., "Immobilized Photosensitisers for antimicrobial applications," Journal of Photochemistry and Photobiology, 2015, vol. 150, pp. 11-30.
Wakayama, Nobuko I. et al., "Magnetic Acceleration of Inhaled and Exhaled Flows in Breathing," Japanese Journal of Applied Physics, 2000, vol. 39, pp. L262-L264.
Matsui, Aya et al., "Real-Time Near-Infrared Fluorescence-Guided Identification of the Ureters using Methylene Blue," Surgery, 2010, vol. 148, No. 1, pp. 78-86.
Ogilby, Peter R., "Singlet oxygen: There is indeed something new under the sun," Chemical Society Reviews, 2010, vol. 39, No. 8, pp. 3181-3209.
Klasse, P.J., "Molecular determinants of the ratio of inert to infectious virus particles," Progress in Molecular Biology and Translational Science, 2015, vol. 129, pp. 285-326.
Prausnitz, Mark R. et al., "Microneedle-based vaccines," Vaccines for Pandemic Influenza, Current Topics in Microbiology and Immunology, 2009, vol. 333, pp. 369-393.
Fracalossi, Camila et al., "Singlet oxygen production by combining erythrosine and halogen light for photodynamic inactivation of *Streptococcus mutans*," Photodiagnosis and Photodynamic Therapy, 2016, vol. 15, pp. 127-132.
Noimark, Sacha et al., "Light-activated antimicrobial surfaces with enhanced efficacy induced by a dark-activated mechanism," Chemical Science, 2014, vol. 5, pp. 2216-2223.
Noimark, Sacha et al., "Incorporation of methylene blue and nanogoid into polyvinyl chloride catheters; A new approach for light-activated disinfection of surfaces," Journal of Materials Chemistry, 2012, vol. 22, Iss. 30, pp. 15388-15396.
Waldman, Robert H. et al., "Immunization Against Influenza: Prevention of Illness in Man by Aerosolized Inactivated Vaccine," JAMA, 1969, vol. 207, No. 3, pp. 520-524.
Sharma, Rashmi et al., "Natrual Edible Olis: Comparative Health Aspects of Sesame, Coconut, Mustard (Rape Seed) and Groundnut (Peanut) A Biomedical Approach," Biomedicai Journal of Scientific & Technical Research, 2017, vol. 1, Iss. 5, pp. 1375-1377.
LFA Tablet Presses, "Tablet Binders," https://www.lfatabletpresses.com/articles/tablet-binders, Accessed: Dec. 6, 2021, pp. 1-8.
Midden, Robert W. et al., "Singlet Oxygen Generation for Solution Kinetics: Clean and Simple," Journal of the American Chemical Society, Jun. 1983, vol. 105, No. 13, pp. 4129-4135.
Plotino, G. et al., "Photodynamic therapy in endodontics," International Endodontic Journal, Jun. 2019, vol. 52, Issue 6, pp. 760-774.
Meller, David M. et al., "Photodisinfection Therapy: Essential Technology for Infection Control," The Infection Prevention Strategy, Jan. 2020, https://infectioncontrol.tips/2020/01/17/photodisinfection-therapy/, Accessed: Jun. 7, 2022, pp. 1-13.
"What is Photodisinfection?," Ondine Biomedical Inc., https://ondinebio.com/technology/, Accessed: Jun. 7, 2022, pp. 1-4.
Almeida, Adelaide et al., "Phage Therapy and Photodynamic Therapy: Low Environmental Impact Approaches to Inactivate Microorganisms in Fish Farming Plants," Marine Drugs, 2009, vol. 7, No. 3, pp. 268-313.
Hasenleitner, Martina et al., "In the Right Light: Photodynamic Inactivation of Microorganisms Using a LED-Based Illumination Device Tailored for the Antimicrobial Application," Antibiotics, Dec. 2019, vol. 9, pp. 1-13.
Trempolec, Natalia et al., "Photodynamic Therapy-Based Dendritic Cell Vaccination Suited to Treat Peritoneal Mesothelioma," Cancers, Feb. 2020, vol. 12, pp. 1-16.
International Search Report and Written Opinion for International Patent Application No. PCT/US2021/046419 dated Feb. 2, 2022, pp. 1-11.
International Search Report and Written Opinion for International Patent Application No. PCT/US2021/048444 dated Feb. 1, 2022, pp. 1-14.
International Search Report and Written Opinion for International Patent Application No. PCT/US2021/046416 dated Nov. 8, 2021, pp. 1-9.
International Search Report and Written Opinion for International Patent Application No. PCT/US2021/046417 dated Nov. 30, 2021, pp. 1-11.
International Search Report and Written Opinion for International Patent Application No. PCT/US2021/046722 dated Dec. 6, 2021, pp. 1-9.
International Search Report and Written Opinion for International Patent Application No. PCT/US2021/058678 dated Jan. 25, 2022, pp. 1-9.
Gonzalez, Murielle, "Hartalega: Expansion plan on track," Cleanroom Technology, 2019, https://cleanroomtechnology.com/news/article_page/Hartalega_Expansion_plan_on_track/153507, Accessed: Apr. 6, 2022, pp. 1-4.

\* cited by examiner

MICROBIAL DISINFECTION FOR PERSONAL PROTECTION EQUIPMENT

CROSS-REFERENCES TO RELATED APPLICATIONS

This application claims the benefit of U.S. Provisional Application No. 63/192,980, filed on May 25, 2021, and U.S. Provisional Application No. 63/113,060, filed Nov. 12, 2020, both applications are incorporated herein expressly by reference.

BACKGROUND

Infectious disease outbreaks and pandemics which are caused by microbial particles such as viruses or other infectious microorganisms necessitate the need for and use of personal protective equipment (PPE) by healthcare workers and staff in medical settings involved with care of, or potentially exposed to infected patients. The actual use of PPE can be highly variable depending on practice patterns and the availability of various types of PPE such as a head covering, a facemask, a face shield, a gown, or shoe coverings. Also, in non-medical settings, face coverings of various types may not be used at all. For the general public, the most common type of PPE is a face covering for at least the nose and mouth to reduce the risk of infection by providing a physical barrier and/or a filtration function to infectious microorganisms suspended in the air and/or transmitted by hand to face contact. Unfortunately, the amount of protection against infection afforded by these generally available PPE face coverings is variable due to the widely varying levels of filtration and barrier materials that are employed. Additionally, even when a user is properly wearing one or more types of PPE that provide a high level of filtration effectiveness and/or relatively non-porous barriers against infectious microorganisms, the user can still become infected when exposed to high-risk environments, such as hospitals and clinics, where prolonged contact with infected patients can occur.

Furthermore, PPE that has a high level of effectiveness is often difficult and cumbersome to wear properly. Also, many types of publicly available face coverings that provide a low level of filtration effectiveness and/or somewhat porous barriers may also be poorly tolerated for long periods of continuous use by wearers/users. The physical contact of a facemask on and over a face of a user can injure the facial skin, impede voice communication, impair respiration (breathing), and generally feel uncomfortable to the user especially when the facemask is properly (tightly) held against the user's face. Facemasks can be particularly uncomfortable in hotter climates and children may not tolerate wearing a facemask despite the recommendation of authorities of institutions, such as schools, sports programs, or the like. Other users may object to wearing a facemask on philosophical grounds or in the mistaken belief that facemask usage is ineffective for prevention of infections. There is a need for PPE alternatives which are more comfortable to a user while still being effective at the prevention of infection, normalizing verbal communication and breathing, and which are likely to be acceptable to wear or use for at least a majority of the general population.

Bleach and/or alcohol-based products are often used for disinfection. However, these products may be toxic when they come in contact with a user's skin or lungs or are ingested. Thus, there is also a need for disinfection products suitable for a variety of pathogenic microbial and viral exposure situations and settings based on active antimicrobial and antiviral disinfection. The disinfection products can affect the air or surfaces.

DETAILED DESCRIPTION OF THE INVENTION

Figure 1A:
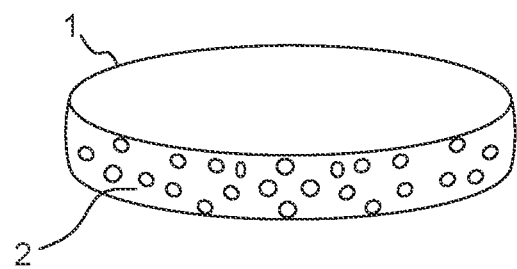
FIG. 1A illustrates one embodiment of an article containing a photosensitizer formulation, e.g., in the form of granulated particles.

The present invention now will be described more fully hereinafter with reference to the accompanying drawings, which form a part hereof, and which show, by way of illustration, specific embodiments by which the invention may be practiced. This invention may, however, be embodied in many different forms and should not be construed as limited to the embodiments set forth herein; rather, these embodiments are provided so that this disclosure will be thorough and complete, and will fully convey the scope of the invention to those skilled in the art. Among other things, the present invention may be embodied as methods or devices. Accordingly, the present invention may take the form of an entirely hardware embodiment, an entirely software embodiment or an embodiment combining software and hardware aspects. The following detailed description is, therefore, not to be taken in a limiting sense.

Throughout the specification and claims, the following terms take the meanings explicitly associated herein, unless the context clearly dictates otherwise. The phrase "in one embodiment" or "in at least one embodiment" as used herein does not necessarily refer to the same embodiment, though it may. Similarly, the phrase "in another embodiment" as used herein does not necessarily refer to a different embodiment, though it may. As used herein, the term "or" is an inclusive "or" operator and is equivalent to the term "and/or," unless the context clearly dictates otherwise. The term "based on" is not exclusive and allows for being based on additional factors not described unless the context clearly dictates otherwise. In addition, throughout the specification, the meaning of "a," "an," and "the" include plural references. The meaning of "in" includes "in" and "on."

The following briefly describes the embodiments of the invention to provide a basic understanding of some aspects of the invention. This brief description is not intended as an extensive overview. It is not intended to identify key or critical elements, or to delineate or otherwise narrow the scope. Its purpose is merely to present some concepts in a simplified form as a prelude to the more detailed description that is presented later.

It shall be understood that the term "microbial", as used herein refers to an infectious microorganism, pathogen, or agent, including one or more of a virus, viroid, bacterium, archaea, protists, protozoan, prion, fungus, or the like.

Further, it shall be understood that the term "immunogen", as used herein refers to an antigen or any other substance that induces both an immune response by a patient's immune system and generation of antibodies that bind to the immunogen.

Briefly stated, various embodiments includes articles, compositions, formulations, or the like that produce singlet oxygen from molecular oxygen using a photosensitizer that is activated using light. Singlet oxygen (often denoted as $^1O_2$) is an excited form of molecular oxygen and distinguishable from the triplet ground state of molecular oxygen. Singlet oxygen is unstable but has a relatively low rate of decay under typical ambient temperatures and pressures. Singlet oxygen is highly reactive and can be used for microbicidal effect, as described herein.

The articles, compositions, or the like described herein utilize a photosensitizer formulation with one or more photosensitizers that, when activated by absorbed light, generate singlet oxygen from molecular oxygen or generate one or more other reactive species which are microbicidal (for example, virucidal). In at least some embodiments, this process is known as photodynamic therapy (PDT). It is understood in this disclosure that singlet oxygen or other reactive species are generated via one or more photoreactions. In at least some embodiments, the generated singlet oxygen or other reactive species produce antimicrobial action by, for example, binding to lipids, proteins, nucleic acids, or other microbial constituents or structures. In at least some embodiments, the microbicidal action is the result of reaction of singlet oxygen or other reactive species with lipids, proteins, nucleic acids, and other microbial and cellular constituents leading to organismal disablement or death.

Singlet oxygen is used herein as an example of a photoactivated reactive species. It should be understood that, unless indicated otherwise, "singlet oxygen" can be substituted by any of the other reactive species (or any combination thereof) generated by photoactivation of the photosensitizer formulation.

Any suitable photosensitizer can be used including any known or contemplated photosensitizers. Examples of suitable photosensitizers include, but are not limited to, methylene blue, methylene blue derivatives, chlorophyll, chlorophyll derivatives, compounds with tetrapyrrole constituents, porphyrins, chlorins, bacteriochlorins, phthalocyanines, texaphyrins, prodrugs such as aminolevulinic acid or derivatives thereof, phenothiaziniums, squaraines, boron compounds, photosensitive transition metal complexes, hypericin, riboflavin and other flavins, curcumin, titanium dioxide, psoralens, tetracyclines, erythrosine, indocyanine green, fluorophores such as fluorescein, or the like or any combination thereof.

Any suitable composition of the photosensitizer can be used including, but not limited to, nanocompositions. In at least some embodiments, the photosensitizer or a formulation containing the photosensitizer can include a substance to affect the photodynamic inactivation process, such as, for example, crystal violet, gold nanoparticles, or the like.

In at least some embodiments, the photosensitizer formulation can include a solvent or dispersant, such as water, saline, or any other suitable solvent or dispersant. In at least some embodiments, the photosensitizer formulation is aqueous. In at least some embodiments, a photosensitizer formulation includes one or more surfactants or emulsifiers to facilitate coating (for example, evenly coating) of the photosensitizer formulation on a hydrophobic surface. Example of surfactants or emulsifiers include, but are not limited to, edible or non-toxic surfactants or emulsifiers such as, for example, lecithin, one or more milk proteins, one or more amino acids, monoglycerides, glycerol, sorbitol, sucrose, propylene glycol, polyglycerol, edible food oils (for example, food oils derived from soybeans, coconuts, palm kernels, rapeseed, or the like), or the like or any combination thereof. In at least some embodiments, a ratio of surfactant volume to photosensitizer volume is at least 1:1, 1:2, or 1:3. Other ratios may be used.

In at least some embodiments, the photosensitizer formulation is applied as a foam. In at least some embodiments, the foam may reduce aerosolization or accidental inhalation or reduce spillage (as compared to a liquid formulation.) In at least some embodiments, a foam is created by mixing air into a photosensitizer formulation (which may optionally incorporate a surfactant) contained in a pressurized canister.

The term "photobleaching" refers to the degradation of the photosensitizer molecules by light. Photosensitizer that is degraded can have reduced, or no, photoactivity. In at least some embodiments, degraded photosensitizer can be replaced or renewed by application of new or additional photosensitizer formulation.

Any suitable light source can be used to photoactivate the photosensitizer formulation including, but not limited to, ambient indoor or outdoor light, light emitting diodes (LEDs), lasers, laser diodes, electroluminescent light devices, chemiluminescent and bioluminescent light sources, incandescent light sources, radioluminescent light sources, xenon, or halogen bulbs, or the like or any combination thereof. In at least some embodiments, one or more optical fibers can be used to deliver light from a light source, such as a LED, laser, or laser diode, to a photosensitizer formulation. In at least some embodiments, the light device is battery powered and the batteries may be rechargeable. The light can be administered in any suitable manner including, but not limited to, continuously, intermittently, in a pulsed on-off pattern, or in any other suitable pattern, in a ramp mode from dim to dark or vice-versa, randomly, or the like or any combination thereof.

The spectral output of the light source is selected to overlap the wavelength(s) or waveband(s) of light absorption by the photosensitizer formulation to facilitate photoactivation of the photosensitizer formulation to generate singlet oxygen or other reactive species and produce a microbicidal action.

In at least some embodiments, intermittent light exposure of the photosensitizer formulation may reduce the photobleaching rate of the photosensitizer formulation or prolong useful photoactivation of the photosensitizer, while still maintaining desired microbicidal action or level of microbicidal action.

In at least some embodiments, the photosensitizer formulation is manufactured in a solid form. In at least some embodiments, the solid photosensitive formulation is disposed into a transparent container (for example, a transparent polymeric container) prior to photoactivation. In at least some embodiments, the solid photosensitizer formulation comprises at least one binder such as, for example, a sugar, gelatin, starch paste, cellulose, acacia, tragacanth, or any other suitable binder. In at least some embodiments, the container is optically transparent and can be formed from a polymer or other suitable material that allows effective light transmission for photoactivation of the photosensitizer formulation.

In at least some embodiments, the photosensitizer formulation is granulated. In at least some embodiments, the solid or granular photosensitizer formulation is disposed into an optically transparent container, which can be formed from a polymer or other suitable material. Unless otherwise indicated, the term "optically transparent" or "transparent", as applied to a structure containing a photosensitizer formulation, means that at least 50%, 75%, 90%, or 99% of at least one wavelength of light for photoactivating the photosensitizer formation is transmitted through a boundary (e.g., a wall) of the structure.

In at least some embodiments, the optically transparent container is made of a rigid material so that the container can maintain its shape, for example, a disc, cube, rectangular cuboid, pyramid, or any other suitable regular or irregular shape. In at least some embodiments, the optically transparent container is made of a flexible material to form a container such as a bag or the like. In at least some embodiments, the material of the transparent container is selected to avoid degradation of the material of the container by action of the photosensitizer formulation (or singlet oxygen or other reactive species generated using the photosensitizer formulation) for an expected useful lifetime or product lifetime of the container.

In at least some embodiments, the optically transparent container for a solid or granulated photosensitizer formulation is perforated to allow airflow through the container and yet contain the photosensitizer formulation granules or solids. In at least some embodiments, the perforations are of smaller diameter than the granules (for example, smaller than at least 80, 90, 95, 99 percent or more of the granules.) In at least some embodiments, a granulated photosensitizer formulation, as compared to a powder photosensitizer formulation, can permit larger diameter perforations to be incorporated into the container, which may enable a larger volume of air passage per unit of time. In at least some embodiments, a granulated form of the photosensitizer formulation may have a reduced photobleaching rate due to the self-shielding effect of the layers of photosensitizer that make up the granules.

FIG. 1A illustrates a transparent container 1 (such as a hollow chamber transparent polymeric disc) containing a granulated or solid photosensitizer formulation 2. In at least some embodiments, the transparent container 1 incorporates multiple perforations 3 (FIG. 1B) which permit passage of air (e.g., oxygen) through the upper surface of the transparent container 1. In at least some embodiments, a size (for example, diameter or length) of the perforations is selected based on a size of the granules of the photosensitizer formulation.

Figure 1B:
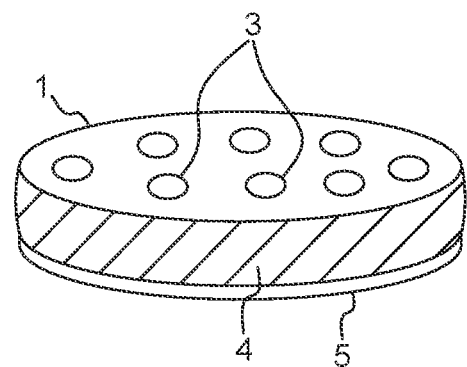
FIG. 1B illustrates another embodiment of an article containing a photosensitizer formulation and having multiple perforations and a filter to facilitate passage of air containing oxygen through the article.

In FIG. 1B, the transparent container 1 contains a photosensitizer formulation in the form of powder 4. The underside of the transparent container 1 includes perforations 3 to allow air passage, but retains the powdered photosensitizer formulation 4, or includes a filter material 5 that permits air passage but retains the powdered photosensitizer formulation 4.

Figure 1C:
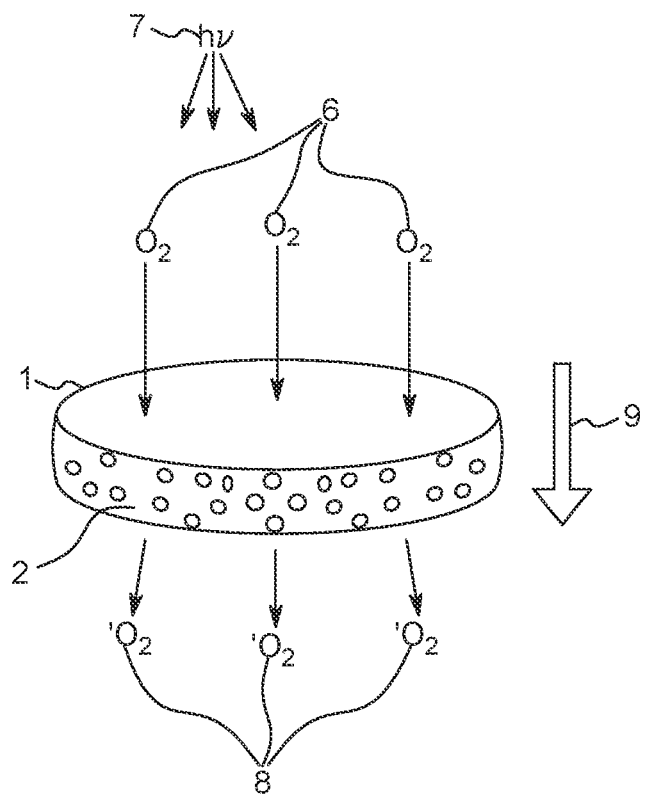
FIG. 1C illustrates passage of molecular oxygen through the article of FIG. 1A to generate microbicidal singlet oxygen.

As illustrated in FIG. 1C, in at least some embodiments, the transparent container 1 allows the flow of ambient air including molecular oxygen 6 through the transparent container and the granulated photosensitizer formulation 2 (or powdered photosensitizer formation 4 of FIG. 1B) disposed therein. Incident light (hv) 7, where ν is the wavelength(s) of the light, interacts with the granular photosensitizer formulation 2 (or powdered photosensitizer formation 4 of FIG. 1B) confined within the transparent container 1 to generate singlet oxygen molecules 8 traveling in the direction of airflow 9.

In at least some embodiments, a device may be coupled to, or positioned near, the transparent container to facilitate airflow through the transparent container and in contact with the photosensitizer formulation. In at least some embodiments, an article includes an antimicrobial assembly with a housing that is air-permeable and a photosensitizer formulation disposed in the housing and an air flow device to generate a flow of air through the antimicrobial assembly. In at least some embodiments, the air flow device is a fan, blower, a bubbler, a propeller of an airborne device (such as a drone), or the like or any combination thereof. In at least some embodiments, the air flow device includes a nozzle and the housing of the antimicrobial assembly includes a cup or cap configured to fit on the nozzle of the air flow device.

Figure 1D:
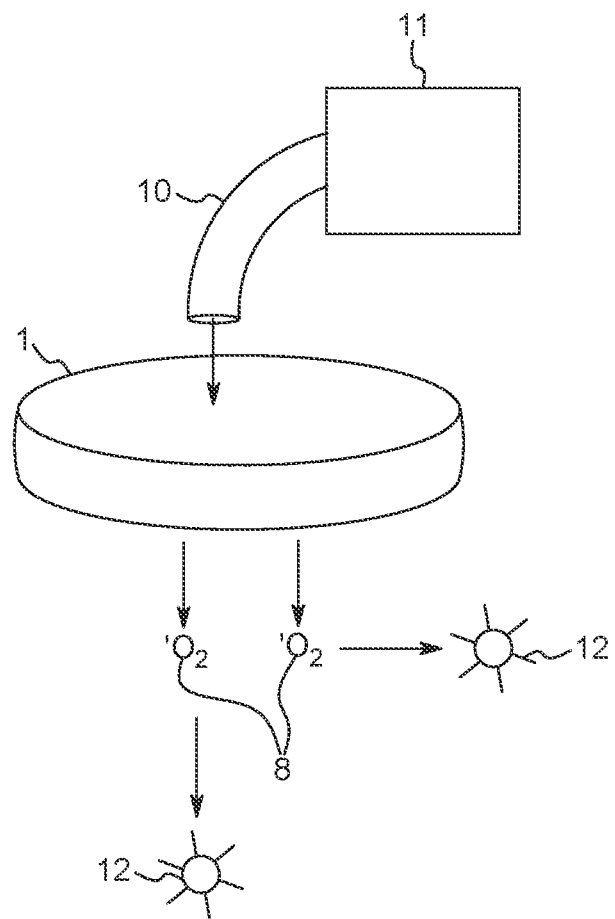
FIG. 1D illustrates one embodiment of an article containing a photosensitizer formulation with a blower to direct air through the article.

FIG. 1D illustrates one embodiment, in which a blower nozzle 10 is connected to blower device 11 and directs the flow air through the transparent container 1 to generate singlet oxygen 8 to destroy or deactivate virus particles 12 or other microbial elements. For example, the singlet oxygen 8 may destroy or deactivate the virus particles 12 or other microbial elements by way of an oxidative process.

Figure 1E:
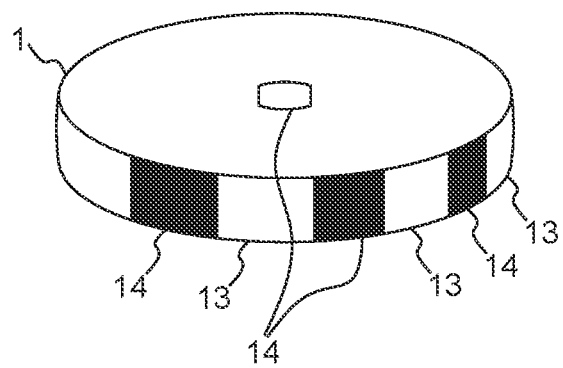
FIG. 1E illustrates one embodiment of an article containing a photosensitizer formulation and one or more light sources to activate the photosensitizer formulation.
Figure 1F:
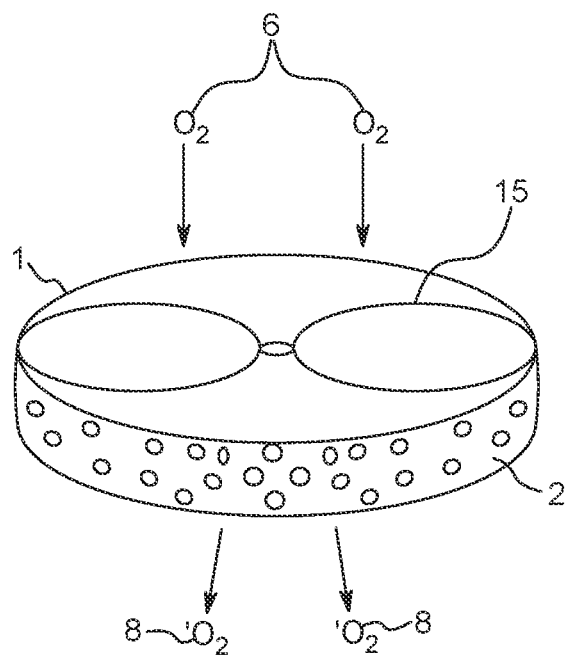
FIG. 1F illustrates one embodiment of an article containing a photosensitizer formulation and a fan to facilitate passage of air containing oxygen through the article.

FIG. 1F illustrates another embodiment in which a fan 15 (for example, a battery-operated fan) is attached to, or positioned near, the transparent container 1 to pull in ambient oxygen 6 and directs the oxygen through the transparent container 1 resulting in an outflow of singlet oxygen molecules 8 into the environment.

In at least some embodiments, the transparent container may incorporate a light source such as a light emitting diode (LED) or array of LEDs. In at least some embodiments, the transparent container is perforated on both surfaces to facilitate the flow of air through the container. In at least some embodiments, the diameter or length of the perforations is selected to prevent or reduce aerosolization of the photosensitizer formulation. FIG. 1E illustrates a transparent container 1 incorporating one or more light sources (for example, LEDs) 13 that emit of light capable of photoactivating the photosensitizer formulation. In at least some embodiments, the light sources 13 are powered by rechargeable or disposable batteries 14.

In at least some embodiments, the photosensitizer formulation is disposed within a container, such as a canister, that also includes a propellant or provides a pressurized system for spraying or otherwise dispensing the photosensitizer formulation.

In at least some embodiments, a polymeric disc (or other object) containing a powdered or granulated photosensitizer formulation has a cup or cap shape. In at least some embodiments, this object fits over a nozzle for directing an air stream such as is commonly found on a commercial passenger jet airplane. In at least some embodiments, the cup or cap incorporates a light source. In at least some embodiments, the cup or cap is provided with a thin air permeable filter which prevents or reduces escape of the powdered or granulated photosensitizer formulation as air passes through the photosensitizer formulation. In at least some embodiments, the cup or cap includes a layer of photosensitizer formulation that is very thin (for example, in a range from 0.0001 millimeters to 1.0 millimeters in thickness.) In at least some embodiments, the cup or cap is removable enabling optional reloading of the photosensitizer powder (for example, by way of a screw top opening) allowing for photosensitizer reloading by a filling device. In at least some embodiments, the cup or cap can be single use or disposable. In at least some embodiments, the photosensitizer formulation is embedded or injected into a filter material that is air permeable and the filter material is placed in the cup, cap, or other object.

In at least some embodiments, the photosensitizer formulation incorporates an antimicrobial preservative to prevent microbial growth within the photosensitizer formulation or the container. In at least some embodiments, the photosensitizer formulation includes a scent. In at least some embodiments, the scent is bergamot, which is used as a pleasing scent, or other compound that is inhalable and can be activated by light (for example, blue light).

In at least some embodiments, the photosensitizer formulation includes riboflavin (vitamin B2). In at least some embodiments, a photosensitizer formulation (for example, a photosensitizer formulation with riboflavin) can used as an application in the eye such as, for example, eyedrops. In at least some embodiments, the photosensitizer formulation can be applied to the conjunctival sac of each eye so that the photosensitizer formulation drains slowly into the nasal cavity, via the nasolacrimal duct, where it can be photoactivated by a light source (for example, a blue light source). In at least some embodiments, the rate of drainage of the administered photosensitizer formulation can be adjusted by altering the viscosity of the photosensitizer formulation. In at least some embodiments, the light source (for example, a blue light source) is at least one LED positioned, for example, just inferior to the bridge of the nose to transilluminate the nasal cavity. Such an arrangement may be useful to, for example, provide disinfection, deactivation, or destruction of airborne pathogens and viruses inhaled through the nose. In at least some embodiments, ambient light may also photoactivate the riboflavin on the conjunctiva. Such an arrangement may be useful for disinfection, deactivation, or destruction of viruses or other microbes on the eye surface, which is a known route of viral transmission (for example, transmission of the SARS-CoV-2 virus.)

Figure 1G:
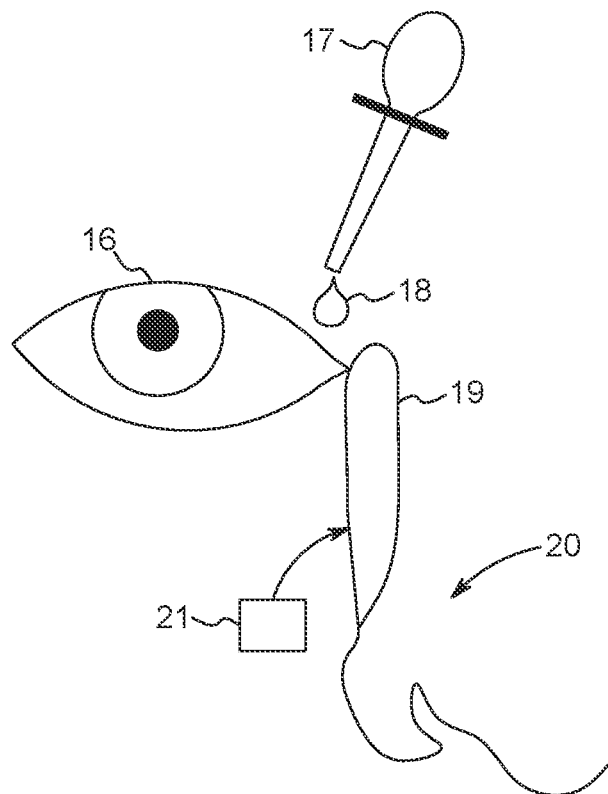
FIG. 1G illustrates applying eyedrops containing a photosensitizer formulation to an eye of a user to direct the photosensitizer formulation into the sinuses and nose where the photosensitizer formulation is activated using a light source.

FIG. 1G illustrates an eye 16 and a dropper 17 which can be used to dispense eye drops 18 containing a photosensitizer formulation (for example, a photosensitizer formation containing riboflavin.) In at least some embodiments, the photosensitizer formulation 18 can be instilled into the conjunctival area, where it can migrate into the duct 19 leading to the nasal cavity 20. The photosensitizer formulation in the nose can be activated by light from a light source (for example, a blue light LED 21) on the nasal skin surface, leading to virucidal or microbicidal action within the nose where infection can occur.

In at least some embodiments, a battery powered LED array is mounted on a frame of a pair of glasses (for example, on a medial and inferior aspect of the frame), aiming light into the nasal cavity by incorporating a lens on or near the LEDs. A battery can be incorporated into the frame to power the LED array.

In at least some embodiments, riboflavin is incorporated into a mouthguard or in the form of a chewing gum. In at least some embodiments, the chewing gum is formulated for time release of riboflavin into the oral cavity. A light source (for example, a blue LED) can be positioned intraorally (for example, attached to the mouthguard or to another oral device) to photoactivate the riboflavin. Other photoactivated compounds can be used instead of riboflavin in these embodiments.

In at least some embodiments, a high molecular weight (HMW) hyaluronic acid formulation (for example, a hyaluronic acid formulation with a molecular weight of at least 500 kDa) is combined with riboflavin or any other suitable photosensitizer. In at least some embodiments, the photosensitizer has a concentration in a range from 0.001 micromolar to 200.0 micromolar. This composition can be exposed to a light source (for example, a blue light source) for photoactivation. In at least some embodiments, the composition can be exposed to ambient light or sunlight for photoactivation.

In at least some embodiments, a formulation containing the HMW hyaluronic acid formulation and a photosensitizer (such as riboflavin) is prepared for application to skin to promote skin hydration. For example, such a composition may reduce the need for extra hand and skin moisturization as may be needed after use of disinfectant alcohol solutions which can dry and irritate skin and hands. Unlike alcohol solutions which are not typically used on the face, in at least some embodiments, the composition of the HMW hyaluronic acid formulation and a photosensitizer (for example, riboflavin) can be used safely on skin surfaces such as the face repeatedly.

In at least some embodiments, a photosensitizer, such as riboflavin, is combined with high molecular weight hyaluronic acid in a gel formulation. In at least some embodiments, a photosensitizer, such as riboflavin, is combined with high molecular weight hyaluronic acid and used as a hair disinfectant (for example, formulated as hair shampoo.)

The photosensitizer formulation can be applied to a variety of different products including, but not limited to, paper products, nets, meshes, screens, woven articles, clothing, garments, cloth articles, or the like or any combination thereof. The following description provides a number of different products and product arrangements that can incorporate the photosensitizer formulation in one or more elements of the product or product arrangement. It will be understood that the photosensitizer formulation is applied or otherwise disposed on at least one element of each of these product or product arrangements even though not explicitly described in the text below. Each of these products or product arrangements is intended to produce singlet oxygen or other reactive species using the photosensitizer formulation on the one or more elements of the product or product arrangement.

In at least some embodiments, the photosensitizer formulation is applied to paper products, skin wipes used for skin cleansing, tissues for nasal clearing and nose blowing, toilet paper, paper towels for hand drying, or facial wipes. Reusable, washable materials incorporating photosensitizer formulations can be manufactured for cleaning surfaces and for skin disinfection. Towels and face cloths incorporating a photosensitizer formulation can be used for example, for skin disinfection or drying of wet skin.

Ultrasound can also be used to activate photosensitizers. This has been referred to as sonodynamic therapy. An ultrasound transducer can be positioned near a photosensitizer formulation to activate the photosensitizer. As an example, in at least some embodiments, an ultrasound transducer is affixed to the underside of the chin. For example, a strap in the shape of a loop can be positioned around each ear with the transducer held under the chin by tension on the straps around the ears. Alternatively, the ultrasound transducer can be affixed under using a medical grade temporary adhesive. In at least some embodiments, the transducer can be powered by a small, rechargeable battery incorporated into the ultrasound transducer mechanism.

In at least some embodiments, a photosensitizer formulation can be used to clean garments, clothing, socks, or the like. The photosensitizer formulation can be added to a washing machine or other cleaning device separately or as part of a detergent composition (or other composition.) In at least some embodiments, the photosensitizer formulation includes at least one of methylene blue, riboflavin, erythrosine, or the like or any combination thereof. In at least some embodiments, the photosensitizer formulation is an aqueous formulation, a powder formulation, or a tablet formulation. In at least some embodiments, the concentration of the photosensitizer ranges from 0.001 micromolar to 100.0 micromolar. In at least some embodiments, a light source is incorporated into the washing machine or other cleaning device. In at least some embodiments, a light source (for example, a LED device contained within a polymeric transparent shell) is inserted into the washing machine or other cleaning device and tumbles in the washing machine or other cleaning device to expose the photosensitizer formulation to the light in order to disinfect the garments, clothing, socks, or the like.

In at least some embodiments, hard or soft sports equipment not suitable for washing in a standard washing machine can be placed in an appropriately sized rotating drum. The drum can be manually powered or motorized and can be sized specifically to accommodate the equipment to be disinfected. In at least some embodiments, the drum is lined with light sources (for example, one or more arrays of LEDs) which provide illumination to all surfaces of the sports equipment. In at least some embodiments, a light source (for example, a LED device contained within a polymeric transparent shell) is inserted into drum. The light sources photoactivate a photosensitizer formulation which is applied (for example, as a spray) on the sports equipment or inside the drum which contains the sports equipment to be disinfected. In at least some embodiments, the spray is automatically applied under pressure from a refillable reservoir incorporated in the drum. As the drum rotates, the light sources serve to photoactivate the photosensitizer formulation on the surfaces of the equipment to be disinfected, as the equipment tumbles. The speed of rotation can be selected to provide light exposure while reducing impact damage to the equipment.

In at least some embodiments, the photosensitizer formulation can be applied using a roll-on device. For example, the photosensitizer formation can be stored in a light-proof or darkened container and a roller (for example, a roller ball or a cylinder) can be attached to the container. In at least some embodiments, the mouth of the light-proof container and the roller diameter are selected for one or more properties, such as, for example, application speed or ease of application to a surface. Examples of surfaces that can receive the photosensitizer formulation from the roll-on device include, but are not limited to, mask surfaces, gloves, netting or mesh, clothing or garments, head coverings or hats, face shields, or the like. In at least some embodiments, the light-proof container is made of non-reactive, light-proof polymer or glass. In at least some embodiments, the light-proof container can be refilled with the photosensitizer formulation using a cap located, for example, at a base of the container. In at least some embodiments, the roller is removed to refill the light-proof container. In at least some embodiments, the base of the container is flared for stability of the container in the upright position. In at least some embodiments, the light-proof container has a rectangular cuboidal, cubic, pyramidal, or cylindrical shape for stability. In at least some embodiments, the roller is in the shape and configuration of a cylinder which can spread the photosensitizer formulation. In at least some embodiments, a liquid compartment is separated from a photosensitizer formulation supplied as a powder. The photosensitizer formulation is admixed with the liquid prior to application using the roller.

In at least some embodiments, the roll-on device is used to apply a photosensitizer formulation (for example, a formulation containing hyaluronic acid or riboflavin) to a user's face or other skin surfaces. In at least some embodiments, a photosensitizer formulation (for example, a formulation containing hyaluronic acid and riboflavin) is applied to the user's hair or hairless scalp to disinfect the hair or scalp surface.

In at least some embodiments, the photosensitizer formulation is contained in a preservative-free container (for example, a spray or pump container) to reduce the need for antimicrobial excipients which could act as singlet oxygen quenchers.

In at least some embodiments, a photosensitizer formulation (for example, a formulation containing methylene blue, erythrosine, or riboflavin or any combination thereof) is applied to the inner surface of a face mask or face covering. In at least some embodiments, the photosensitizer formulation has a photosensitizer concentration ranging from 0.000001 to 1000.00 micromolar. In at least some embodiments, a photosensitizer formulation (for example, a formulation containing methylene blue, erythrosine, or riboflavin or any combination thereof) is applied to the outer surface of a face mask or face covering. This application can include the rim of the face mask or face covering where air leakage upon inspiration and exhalation can occur. Singlet oxygen generated in the air around the face mask or face cover rim can disinfect air, which is potentially microbial contaminated, and leaking around the rim. In another embodiment, methylene blue or any other suitable photosensitizer is applied to the inner mask surface closest to the mouth and nose at a concentration that is below any potential toxic inhalational range. In at least some embodiments, this photosensitizer formulation has a photosensitizer concentration ranging from 0.001-10.0 micromolar.

In at least some embodiments, a manual or powered, wide surface sprayer can be used to apply a photosensitizer formulation to a PPE surface area larger than a typical face mask or face cover, such as a gown, a head cover, shoe covers, face shields, or the like.

In at least some embodiments, the photosensitizer formulation is applied to a film. In at least some embodiments, the film is dark or light-proof and may be polymeric. In at least some embodiments, the film may be pre-applied to a surface, such as a mask surface, a net, or a mesh. In at least some embodiments, the film covers the photosensitizer formulation to prevent or reduce light activation and avoid photobleaching or photodegradation of the photosensitizer. The film can be removed leaving a coating of the photosensitizer formulation on the surface. The surface optionally has a sticky or electrically charged surface (for example, an electret material) that attracts the photosensitizer molecules to the surface to be disinfected.

In at least some embodiments, the photosensitizer formation is applied between two films and one of the films is attached to the surface. The other film can be removed to expose the photosensitizer formulation.

In at least some embodiments, titanium dioxide, optionally in combination with one or more other photosensitizers, is applied to a mask, headwear, netting, a gown, other garment, or other surface to enable long lasting photodisinfection. Titanium dioxide is a photocatalyst that is not prone, or less prone, to photobleaching.

In at least some embodiments, a titanium dioxide layer is separated by a thin film from a photosensitizer formulation layer to reduce inactivation of the photosensitizer formulation by the titanium dioxide layer.

In at least some embodiments, the photosensitizer formulation is provided in a semi-solid form by adding a solidifying excipient to facilitate application of the photosensitizer formulation to any surface. For example, the photosensitizer formulation and excipient can be incorporated into a stick form similar to a deodorant product.

In at least some embodiments, the photosensitizer formulation incorporates an ultraviolet (UV) light absorber, such as a UV absorber used in sunscreens or the like. The presence of a UV absorber can reduce photobleaching in outdoor light or other lighting containing UV light.

In at least some embodiments, a photosensitizer formulation is coated on paper or a paper product. In at least some embodiments, the paper is air permeable. In at least some embodiments, the coated paper or paper product can be used as a disposable barrier screen. For example, the barrier screen can be used around an infected coughing patient to protect others from airborne infectious droplets and aerosols. In at least some embodiments, the paper can be cut into desired dimensions to fit a desired location and position and attached to dowels or rods using tape, glue, or hook and loop tape and fasteners or any other suitable fastener. In at least some embodiments, a kit could also include linear sleeves and cornering sleeves and supporting stands which accommodate the ends of the dowels or rods enabling custom assembly of screens into free standing barriers. These barriers can be linked to provide all-around protection or directional protection.

In at least some embodiments, the photosensitizer formulation is a dry powder. In at least some embodiments, the powder is confined within a chamber (for example, a polymeric chamber) with any suitable shape (for example, a disc, sphere, cylinder, cube, rectangular cuboid, or the like). In at least some embodiments, the chamber is optically clear, and perforated such that air passes, but confines the powdered photosensitizer formulation within the disc. In at least some embodiments, filter material, which is preferably transparent to light, is incorporated into the chamber to provide a barrier for the powder that is also permeable to air and light. The chamber provides a barrier to viral or microbial passage by action of the photosensitizer formulation to create singlet oxygen. Any suitable filtration material can be used such as, for example, polypropylene. In at least some embodiments, the filter material is disposed on the upper and lower surfaces of the chamber or is confined within the air and light permeable chamber.

In at least some embodiments, a light source (for example, at least one battery powered LED) is incorporated into, or attached to, the chamber. In at least some embodiments, the light source is coupled to at least one optical fiber extending into the chamber to aid in light distribution within the chamber.

In at least some embodiments, air is passed through the chamber containing the photosensitizer formulation (which may incorporate a microbial filter) under pressure. In at least some embodiments, the chamber is placed in front of a fan or a blower for continuous disinfection of a large volume of air. In at least some embodiments, a fan or blower (which may be battery-powered) is incorporated into the chamber. Such an arrangement may provide a self-contained, portable singlet oxygen generator.

In at least some embodiments, the photosensitizer formulation is in the form of a solid cake, a granular composition, or a power contained in an air-permeable transparent filter insertable into a chamber or other container.

The photosensitizer formulation can be applied to or otherwise disposed on a mask, net, mesh, screen, or other object to generate singlet oxygen or other reactive species to provide an microbicidal effect as described above. A variety of different products and product arrangements are described below that utilize a mask, net, mesh, screen, or other object with the photosensitizer formulation applied or otherwise disposed thereon. It will be understood that at least one mask, net, mesh, screen, or other object of the products and product arrangements described below has the photosensitizer formulation applied or otherwise disposed thereon for generation of singlet oxygen or other reactive species.

Figure 6A:
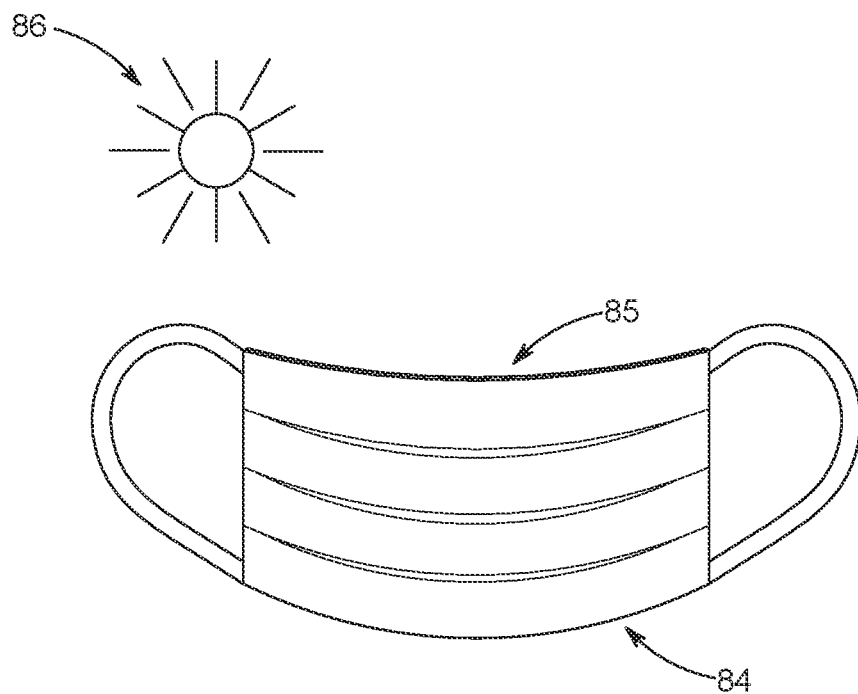
FIG. 6A illustrates one embodiment of a face cover or mask with a photosensitizer formulation illuminated by an external light source.
Figure 6B:
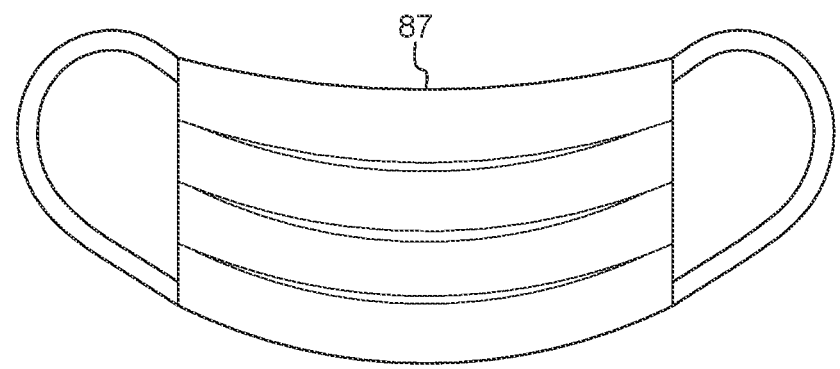
FIG. 6B illustrates one embodiment of a mask with a functionalized graphene sensor.
Figure 6C:
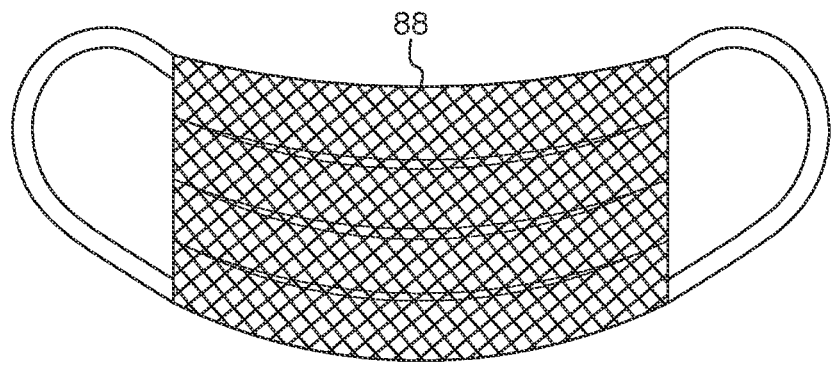
FIG. 6C illustrated the mask of FIG. 6B exposed with the sensor activated.

FIG. 6A illustrates an external light source 86 which illuminates a photosensitizer formulation 85 incorporated, embedded, or applied to a face cover or mask 84. FIGS. 6F and 6G illustrates the exterior and interior, respectively, of a mask 92 that includes a transparent window 91.

In at least some embodiments, an immobilized photosensitizer formulation is disposed on a surface. In at least some embodiments, the photosensitizer formulation is disposed in different concentrations on the surface. In at least some embodiments, the concentration of the photosensitizer formulation on the surface is graduated from a lower to a higher concentration of the photosensitizer formulation. The surface can be, for example, a surface of a mask, net, mesh, or any other suitable object that is proximate to a user. The ambient light (or a light source incorporated in, or near, the object) induces photoactivation of the photosensitizer formulation and production of varying amounts of singlet oxygen. In at least some embodiments, microorganisms, such as viruses, that adhere to, or are in close proximity to, the surface coated with the photosensitizer formulation are damaged or degraded to different extents. In at least some embodiments, the damage or degraded microorganism may result in the generation of antigenic fragments that can be directly or indirectly administered as immunogens to the user. In at least some embodiments, the microorganism that is damaged or degraded can be used to generate an effective repertoire of antigens in this way. These antigens may be inhaled by a user who is wearing a treated mask or net/mesh as a face covering. The photosensitizer formulation reduces whole microorganism passage but may not prevent smaller microbial fragments and antigens passing through to the user's mouth or nose. An object placed in proximity to the user's head or face can serve the same function.

In at least some embodiments, a light source incorporated in, or near, the mask, net, mesh, or other object can provide a variable amount of photoactivation to produce a varying amount of singlet oxygen at varying rates. In at least some embodiments, the variable degree of singlet oxygen production provides for the production of a range of antigenic fragments which may be immunogenic when inhaled by the user.

In at least some embodiments, varying amounts of a photosensitizer formulation are applied in specific segments to the mask, net, mesh, or other object that is proximate to the user's face. In ambient light, or using an incorporated or proximate light source, different degrees of microbial and viral degradation will occur leading to creation of viral fragments and antigens, some of which may lead to a beneficial immune stimulation reaction when inhaled by the user.

The advantage of this microbial antigen exposure is that the user is exposed to the exact pathogenic microorganism in an antigenic form that is in the ambient environment around the user. Such exposure may overcome issues that can render vaccines less effective, for example when the vaccine does not match the particular characteristics of the pathogenic microbe, such as can happen with influenza vaccines.

In at least some embodiments, an article includes a substrate; and a photosensitizer formulation disposed on or in the substrate with a concentration gradient of the photosensitizer formation along at least one dimension of the substrate. In at least some embodiments, the substrate is a mask or face covering. In at least some embodiments, the substrate is a net, netting, or mesh. In at least some embodiments, the substrate is a curtain of strands, fibers, or monofilaments. In at least some embodiments, the article further includes a light source incorporated in, or coupled to, the substrate. A kit can include any of these articles and a pair of glasses or other object that incorporates the light source. A kit can include any of these articles and a saliva assay to assess a user response to the antigenic particles.

Figure 8A:
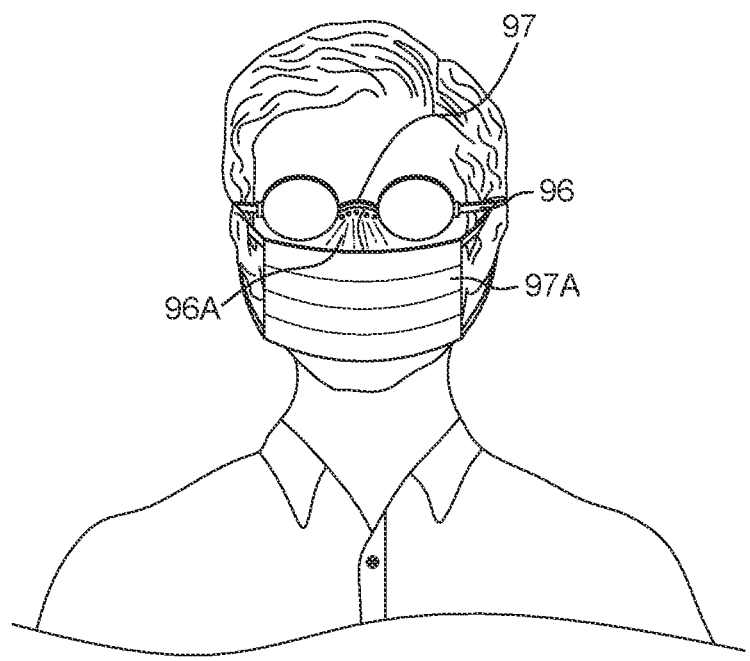
FIG. 8A illustrates one embodiment of glasses or spectacles with an embedded light source proximate to the bridge of the nose which emits light to illuminate a mask.

FIG. 8A illustrates glasses or spectacles 96 with an embedded light source 97 proximate to the bridge of the nose which emits light 96A to illuminate a mask 97A. Light 96A delivers light to the inner and/or outer surface of the mask 97A.

Figure 8B:
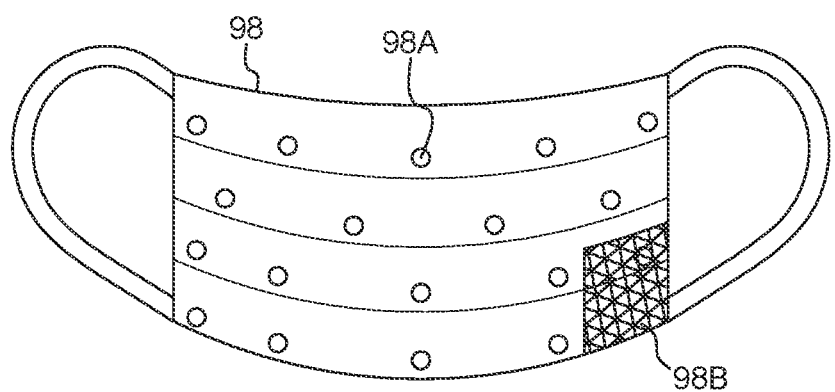
FIG. 8B illustrates one embodiment of a mask with light sources powered by a battery or solar panel.
Figure 8C:
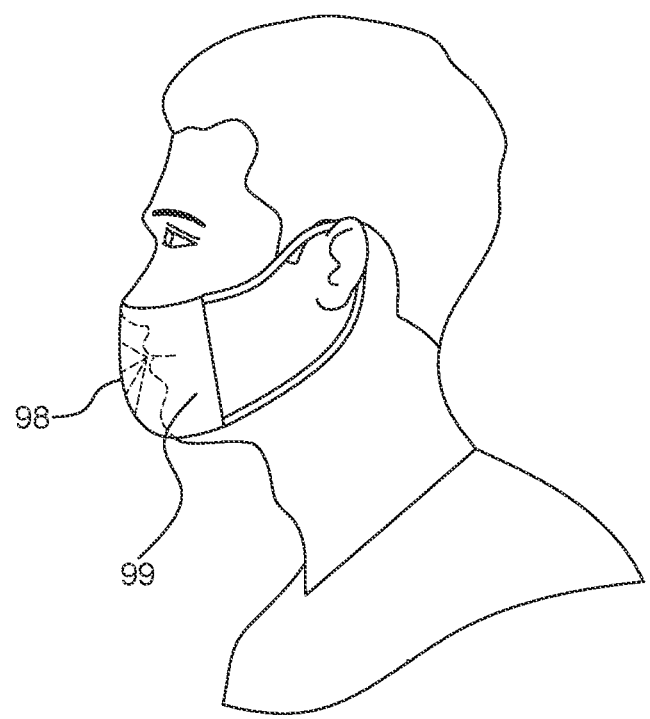
FIG. 8C illustrates the mask of FIG. 8B worn by a user.

FIGS. 8B and 8C illustrate a mask 98 with light sources 98A powered by a battery or solar panel 98B. The light sources illuminate the interior of the mouth when the jaw 99 is opened.

In at least some embodiments, a photosensitizer formulation, such as riboflavin and high molecular weight hyaluronic acid, used on skin surfaces of the user, such as on the face, can also lead to antigenic fragments which can serve as an immunologic stimulator. For example, transfer of the antigenic fragments from hands touching the face with subsequent transfer to the mouth can occur which is a common and known route of infection.

In at least some embodiments, a test kit specific to detection of secretory immunoglobulin A (SIgA) is included with an antiviral product that utilizes a photosensitizer formulation to produce singlet oxygen. This test kit can assess the generation of SIgA on mucosal surfaces. For example, the test kit may be used to collect and analyze SIgA in saliva samples. The SIgA test kit can be used to quantify the generation of SIgA before and after use of the immune stimulation from inactivated viral particles, fragments, or antigens that are generated using the photosensitizer formulation. In at least some embodiments, testing for this trained immunity is assessed after photoactivation. Induction of trained immunity can afford extra protection for the mask user against pathogens, in addition to the induction of SIgA by the acquired immune mechanisms.

Figure 7A:
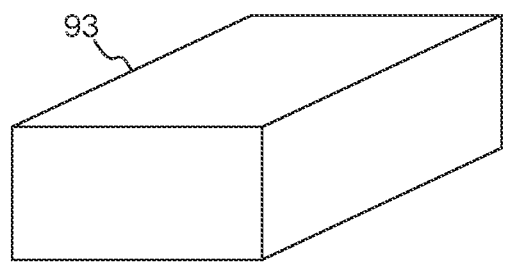
FIG. 7A illustrates one embodiment of a saliva immunoglobulin test kit.
Figure 7B:
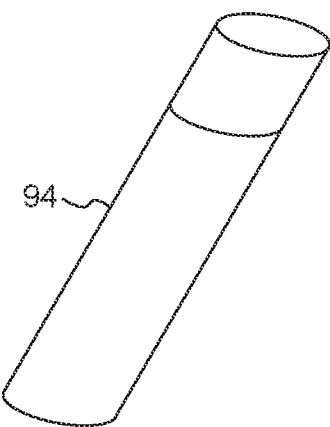
FIG. 7B illustrates one embodiment of a saliva collection tube of the saliva immunoglobulin test kit of FIG. 7A.
Figure 7C:
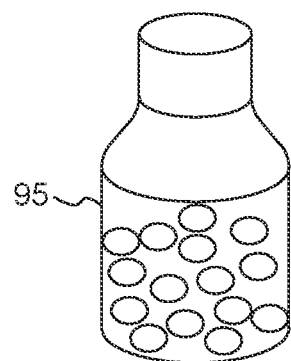
FIG. 7C illustrates one embodiment of a system for analyzing the saliva immunoglobulin test kit of FIG. 7A.

FIGS. 7A to 7C illustrate a saliva immunoglobulin test kit 93 that has a saliva collection tube 94 which is processed and analyzed by a system 95.

In at least some embodiments, an oral formulation of beta glucan, which is a substance found in certain mushrooms, oats, and certain grains, is included in a product kit, and used as an oral immune stimulant to further boost the beneficial immune response to the photodynamically generated viral antigens and degraded virions. In at least some embodiments, oral dosing of beta glucan can range from 10 to 100 mg kg/day.

In at least some embodiments, light delivered to the mucosal surface of the nose and/or mouth is utilized as an adjuvant to increase the immune response to the photodynamically generated viral antigens and degraded virions. In at least some embodiments, a light source incorporated into a mask, face cover, net, screen, mesh, or any other surface proximate to the user's face can be used for the photodynamic generation of viral antigens and degraded virions, as well as an adjuvant, stimulating a beneficial immune response. Light in the red spectrum, for example, delivered to the skin, wounds, or other tissues has immune stimulating effects. Light sources can include, but are not limited to lasers, laser diodes, light emitting diodes, or other semiconductor light sources such as those using quantum dot technology. Light wavebands that encompass the red spectrum from approximately 600 nm to 800 nm are preferred, though spectral light distributions outside of these ranges in the visible and near infrared spectrum can also be useful.

In at least some embodiments, the light delivered to the mucosa can range from 1 to 500 joules/cm$^2$, or in a range from 10 to 250 joules/cm$^2$. In at least some embodiments, multiple intermittent light treatments, for example 1 to 10 treatments/hr or 1 daily treatment, to the mucosa can enhance a beneficial immune response. In at least some embodiments, light is delivered intraorally by an external light source through an open mouth, or by way of an optical diffusing fiber within the oral cavity with the mouth closed around the optical fiber.

Figure 1H:
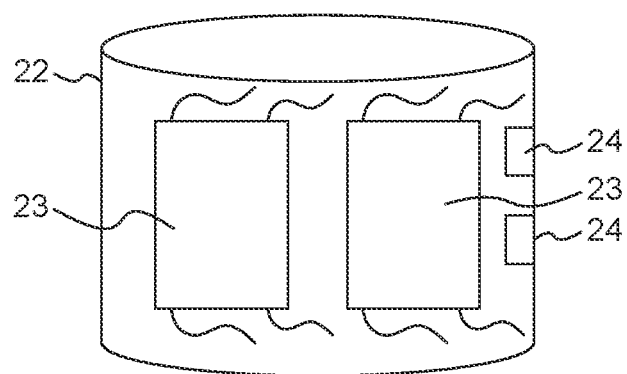
FIG. 1H illustrates one embodiment of a pouch for receiving a face mask and a photosensitizer formulation that is illuminated by a light source to disinfect the face mask.

Any bright light source can be used that emits wavebands or wavelengths of light that are effectively absorbed by the photosensitizer formulation leading to generation of singlet oxygen or other reactive species. As an example, a one micromolar solution of methylene blue is activated by LED based light at a dose of, for example, 120 J/cm one hour to inactivate viruses and bacteria in blood plasma. Any suitable light source can be used including, but not limited to, light emitting diodes (LED), xenon lamps, fluorescent bulbs and tubes, incandescent light bulbs, electroluminescent devices, lasers, or the like or any combination thereof. In at least some embodiments, a light source is incorporated into support structures such as polymeric rods, struts, or the like In at least some embodiments, a disinfection device can contain, and quickly and conveniently disinfect at least one mask or net/mesh. FIG. 1H illustrates one example of a disinfection device that includes a transparent pouch 22 that can accommodate at least one face mask 23, net, mesh, or other item for disinfection. In at least some embodiments, the disinfection light device incorporates a light source 24 (for example, at least one LED) which emits at least one wavelength or waveband of light capable of being absorbed by the photosensitizer formulation used on the mask or net/mesh surface. In at least some embodiments, the disinfection device includes a device housing, such as the transparent pouch 22. The device housing can be made of any suitable polymeric materials. The device housing can be stiff or flexible. The device housing can form a housing for the light source (for example, a rechargeable LED light source) and can receive one or more masks, nets, or meshes within the device housing. In at least some embodiments, the device housing is gas permeable to enable entry of molecular oxygen from the ambient air to produce an effective amount of singlet oxygen. In at least some embodiments, light is diffused over at least a portion of the surface of the mask, net, or mesh surface by the light source or by using at least one optical fiber, or an optical fiber array, coupled to the light source. In at least some embodiments, the disinfection device is dimensioned so that it fits easily into a garment pocket, a purse or handbag, a backpack, a fanny pack, or the like and can be considered a personal disinfection device. In at least some embodiments, a photosensitizer formulation applicator is optionally attached or fixed to the disinfection device using any suitable attachment mechanism including, but not limited to, Velcro®.

In at least some embodiments, the photosensitizer formulation is provided, or dispersed within, the interior of the disinfection device. For example, the photosensitizer can be provided in the form of an aqueous spray (which may incorporate a surfactant or an emulsifier), a dry powder, or a gel. In at least some embodiments, the photosensitizer formulation is administered through an inlet port in the disinfection device that accommodates a nozzle which is part of a refillable container containing the photosensitizer formulation. The nozzle may be used to coat the mask or PPE surfaces with the photosensitizer formulation.

In at least some embodiments, the disinfection device is shaken, rotated, compressed, or otherwise manipulated manually or using a roller to disperse the photosensitizer formulation so that it coats the item, material, or fabric to be disinfected. The light source is then activated which leads to disinfection by photoactivation of the photosensitizer formulation.

In at least some embodiments, the disinfection device is configured to accommodate masks or other objects of various sizes and shape. In at least some embodiments, the disinfection device incorporates a rechargeable battery which powers the light source. In at least some embodiments, the disinfection device includes a flexible solar panel to recharge the battery.

In at least some embodiments, additives are incorporated into the interior of the disinfection device so that the mask, net, mesh, or other object is exposed to the additive(s), Examples of additives include, but are not limited, to, a scented oil or extract, a fragrant substance, or the photosensitizer formulation. In at least some embodiments, the disinfection device incorporates a flexible, compressible reservoir containing the photosensitizer formulation and/or additives in communication with the inner space of the disinfection device. In at least some embodiments, the contents of the reservoir can be discharged by squeezing or compression into the interior of the disinfection device prior to photoactivated disinfection.

In at least some embodiments, the disinfection device incorporates an on-off switch that can be manually or automatically controlled or can be preprogramed to deliver light for a specified, adjustable time period. In at least some embodiments, the disinfection device has an internal capacity that is large enough to accommodate bulkier garments, head coverings, face coverings, gloves, shoe covers, or the like. In at least some embodiments, the disinfection device is foldable into a smaller configuration (for example, a pocket-sized configuration).

In at least some embodiments, the disinfection device enables a user to disinfect at least one mask, net, mesh, PPE, or other object at any time, in any location, or on demand to facilitate reliable reuse of these items by the user. One possible advantage is that after presumed contamination by a pathogenic organism, the mask, net, mesh, PPE, or other object can be immediately disinfected in a rapid fashion, enabling convenient, facile reuse on demand.

In at least some embodiments, the device housing is a flexible polymeric pouch that is affixable or attachable to clothing or garments of a user. In at least some embodiments, a mask, net, mesh, or other PPE can be quickly inserted into the attached pouch for disinfection.

In at least some embodiments, the device housing is a flexible transparent pouch that is large enough to fit over an adult hand and the mask to be disinfected. The pouch is deformable such that an adult hand, right or left can be inserted into the pouch. A mask or PPE can be grasped by a user and the pouch is pulled around the mask followed by spraying or applying the photosensitizer formulation to the mask (or PPE) surfaces and the user's hand. This can be used to disinfect the mask (or other PPE) as well as the user's hand that touched the mask (or other PPE). Alternatively, the mask (or other PPE) is sprayed with the photosensitizer formulation and then placed into the pouch.

In at least some embodiments, the pouch or container of the disinfection device can be sealed using, for example, a resealable zipper lock, a clamp, or any other suitable sealing mechanism. In at least some embodiments, the mouth of a pouch can be manually maintained in an open, circular of ovoid configuration for ease of mask or PPE insertion. In at least some embodiments, the inner surface of the device housing can include a reflective material, such as a metallized or reflective surface coating, Mylar®, or the like, to facilitate more even distribution of light from the light source.

In at least some embodiments, the disinfection device includes at least one sponge containing the photosensitizer formulation in a liquid form. In at least some embodiments, the sponge is compressed (for example, manually compressed) to release the photosensitizer formulation leading to spread on the surface of the mask, net, mesh, PPE, or other object.

In at least some embodiments, a personal pocket-sized illuminator is used by a health care worker or other individual to disinfect a mask, net, mesh, other PPE, or any other suitable object. For example, the disinfecting can be performed between caring for multiple infected patients. In at least some embodiments, the heath care worker can apply an amount of the photosensitizer formulation to the mask, net, mesh, or other PPE prior to insertion into, or application of, the personal illuminator. In at least some embodiments, a larger volume personal illuminator can be deployed to enable disinfection of larger volume garments such as gowns in any location.

In at least some embodiments, a flexible net, netting, or mesh is made using a gas permeable, highly transparent material such as, but not limited to, polypropylene, nylon, polyethylene, polyesters, polyamides, polyvinyl chloride, polyvinyl alcohol, polyimides, cotton, fiberglass, metal manufactured as a mesh, nanomaterial fibers, ceramic fibers, rayons, silk, polyacrylonitrile, or the like or any combination thereof. The net or mesh may incorporate metallic or other types of coatings to impart electret properties. The net, netting, or mesh may include one or more coatings to impart or increase hydrophobicity. In at least some embodiments, the net or mesh is manufactured of a material capable of withstanding multiple washings in a standard washing machine. A photosensitizer formulation is applied to the net, netting, or mesh. In at least some embodiments, the net or mesh can be used as, or as part of, a facemask or other face covering.

Figure 1I:
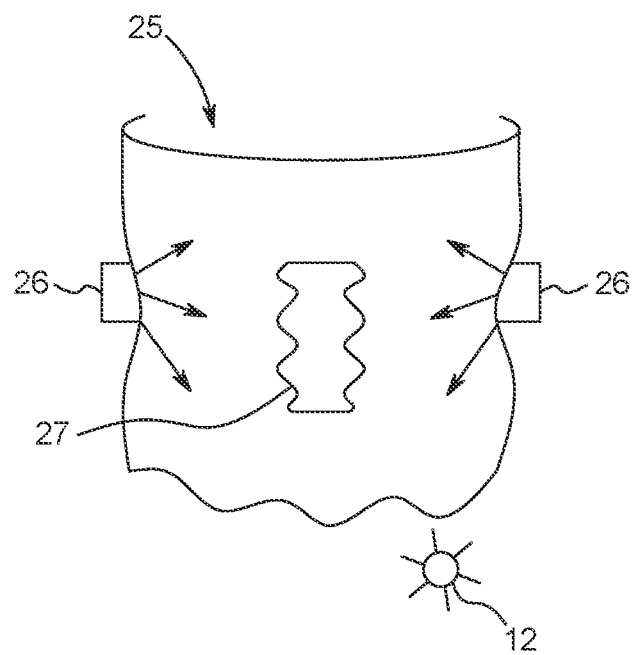
FIG. 1I illustrates one embodiment of a net with an applied photosensitizer formulation that is illuminated by at least one light source.

FIG. 1I illustrates a net 25 with an applied photosensitizer formulation 27. A pathogenic virus 12 (or other microbe) which becomes adherent to the net 25 is inactivated and destroyed by the applied photosensitizer formulation that is photoactivated by LED light 26.

In at least some embodiments, in contrast to conventional facemasks made from opaque materials, the use of transparent materials facilitates or enables viewing of the user's face to detect emotion and facial expression. By the same token, the use of transparent materials can provide the user with an unobstructed view of the external environment. Since materials that are electrets may not be entirely optically clear when in the form of net, netting, or mesh. In at least some embodiments, the net, netting, or mesh can include a light source, such as at least one light emitting diode (LED). In at least some embodiments, the light source includes a battery that may be disposable or rechargeable. In at least some embodiments, the light source is coupled to at least one optical fiber that is incorporated into the structure of the net, netting, or mesh. In at least some embodiments, the optical fiber(s) is/are woven, glued, or thermally bonded to the net or mesh. The light source and optional optical fiber(s) can illuminate the user's face and provide light for photoactivation of a photosensitizer formulation applied to the net or mesh. In at least some embodiments, the light source is located lateral to the face of the user, in a superior location relative to the user's face, or inferior to the user's face.

In at least some embodiments, the net, netting, or mesh includes a lens incorporated into the net, netting, or mesh to facilitate illumination of the user's face by the light source and optional optical fiber(s). In at least some embodiments, a light beam from the light source is positioned (for example, using the lens or the optical fiber(s)) such that light falls upon the user's face and is reflected outwards, thus improving visibility of the user's face. In at least some embodiments, positioning of the light source, optional optical fiber(s), and optional lens is such that the user's eyes are protected from direct illumination from the light source falling upon the user's retinas. In at least some embodiments, the light source provides lighting to highlight specific features of the user's face. In at least some embodiments, the light source produces white light, but other colors of light may be provided by a light source or, at least in some embodiments, the color of the light may be selectable.

Figure 6D:
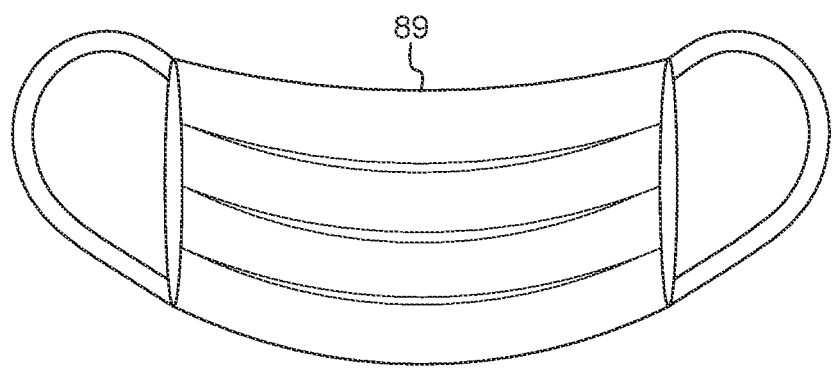
FIGS. 6D and 6E illustrate an outer surface and an interior surface (or vice versa) of one embodiment of a mask incorporating one or more light sources which are powered by a battery to illuminate the interior and/or outer surface of the mask.
Figure 6E:
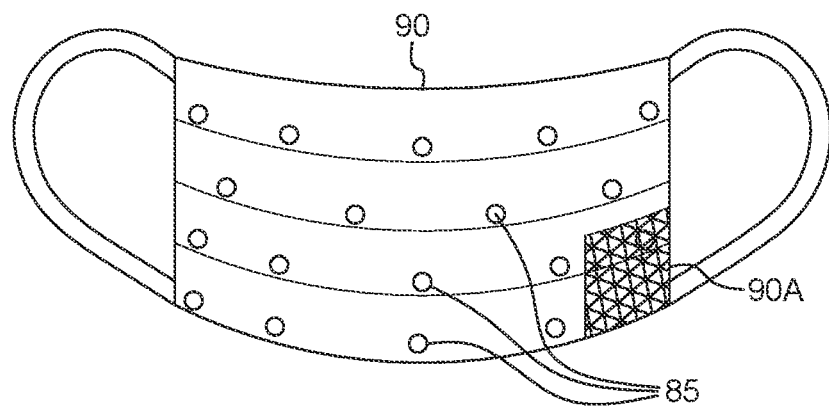
Figure 6F:
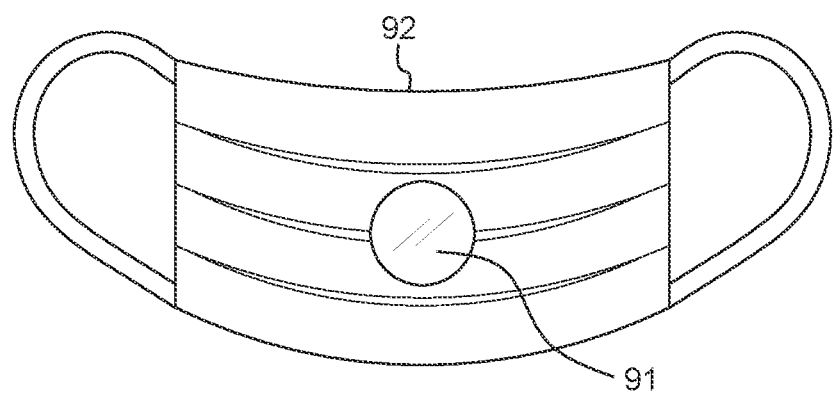
FIGS. 6F and 6G illustrate an outer surface and an interior surface (or vice versa) of one embodiment of a mask incorporating a window.
Figure 6G:
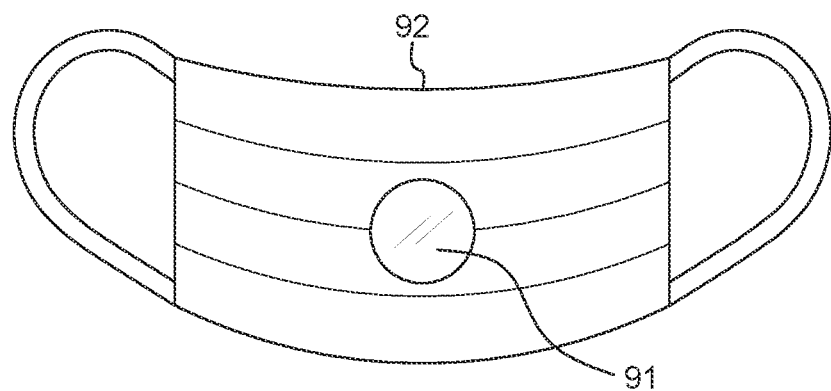

FIGS. 6D and 6E illustrate an outer surface 89 and an interior surface 90 (or vice versa) of a mask incorporating one or more light sources 85 which are powered by a battery 90A which illuminates the interior and/or outer surface 89, 90 of the mask to activate the photosensitizer formulation incorporated, embedded, or applied to the mask.

In at least some embodiments, a non-imaging diffusing lens is incorporated in the center, or off center (by a range of 1.0 mm to 3.0 cm), of a mask or other face covering permitting light to enter the interior of an opaque mask or face covering. The lens may direct light to induce photodynamic action within the mask interior, for example, when the inner lining proximate to the mouth and nose are coated with a photosensitizer formulation.

In contrast to the type of generally uniform netting fibers, strands, or monofilaments which would be used to prevent passage of insects, in at least some embodiments, a net, netting, or mesh incorporates tiny bumps, micro-projections, or hair-like projections in the strands which serve to increase the surface area on which the photosensitizer formulation can be deposited or applied. An increased amount of photosensitizer formulation can increase the amount of singlet oxygen produced and prolong the period of time over which singlet oxygen is produced by reducing the impact of loss of active photosensitizer due to photobleaching. In at least some embodiments, the fibers or strands of the net, netting, or mesh include microscopic pits to increase the surface area of the fibers or strands and increase the amount of photosensitizer formulation that can be deposited or applied to the fibers or strands as compared to a smooth surface.

In at least some embodiments, any of the nets, nettings, or meshes described herein can have 500 to 2000 holes per square inch (for example, 75 to 300 holes per square centimeter.)

In at least some embodiments, a wearable article; a mesh, net, netting, screen, or curtain of strands, fibers, or monofilaments coupled to the wearable article, storable in a stored configuration on or within the wearable article, and deployable to a deployed configuration; and a photosensitizer formulation disposed on or in the mesh, net, netting, screen, or curtain. In at least some embodiments, is a hat, helmet, or other headgear. In at least some embodiments, is a chain or piece of jewelry. In at least some embodiments, the assembly includes a pulley system to return the mesh, net, netting, screen, or curtain from the deployed configuration to the stored configuration. In at least some embodiments, the assembly includes a rod coupled to the mesh, net, netting, screen, or curtain to facilitate deployment of the mesh, net, netting, screen, or curtain.

In at least some embodiments, a head net or face net is coated with a photosensitizer formulation. In at least some embodiments, the head or face net is 5 to 50 cm in length. In at least some embodiments, the head or face net is incorporated into, or attached to, a brim of a hat, a bill portion of a baseball style cap, or a visor style of headwear. In at least some embodiments, the bill of the cap and the visor are interchangeable structures. In at least some embodiments, the head or face net can be folded and compressed in an accordion-like or crinkled arrangement and positioned, for example, around the brim of a hat or on the bill of a cap.

In at least some embodiments, a head net when deployed surrounds the head completely in a 360-degree arc in an arc of at least 90, 135, 180, 200, 225, 240, or 270 degrees. In at least some embodiments, a face net, when deployed, is anterior and lateral to the face, for example, in an arc of at least 90, 120, or 180 degrees. In at least some embodiments, an inferior aspect of the head or face net incorporates a wire around the bottom edge. In at least some embodiments, a string, wire, or chain is attached to the wire. In at least some embodiments, the inferior aspect of the head net or face net contains at least one weight (for example at least one metallic rod which may weigh, for example, 1 to 10 grams) to facilitate deploying or unfurling the head net or face net. In at least some embodiments, when compressed in an accordion-like fashion, a catch mechanism prevents the string, wire, or chain from deploying. In at least some embodiments, the weight of the metallic rod serves to unfurl the head or face net rapidly, due to gravitational pull on the weight, when the catch is released.

In at least some embodiments, a pulley system incorporating a string, wire, or chain enables the user to recompress the head or face net. In at least some embodiments, the pulley system includes a small plastic wheel (for example, 2 to 10 mm in diameter) over which the string, wire, or chain runs. In at least some embodiments, the wheel rotates around an axis formed by a strut incorporated into the hat brim or cap bill laterally, one on each side. In at least some embodiments, the distal end of string, wire, or chain incorporates a bead which is grasped by the user, and when pulled in an inferior direction, compresses the head or face net. In at least some embodiments, the wire, string, or chain runs in a channel, tunnel, or sleeve (for example, 2 to 5 mm in diameter). In at least some embodiments, the channel, tunnel, or sleeve is created by rolling the lateral edges on each side of the face net and attaching the entire long edge creating a tube through which the wire, string, or chain runs. In at least some embodiments, the head net incorporates a channel, tunnel, or sleeve which travels the length of the net laterally on both sides, through which the wire, string, or chain, runs. In at least some embodiments, the distal end of each wire, string, or chain is attached to the wire at the inferior edge of the head or face net. When the wire, string, or chain is pulled by grasping the bead(s), the net is drawn up in a superior direction exposing the face, or only the mouth, so that food can be eaten, and drink can be imbibed. In at least some embodiments, the wire, string, or chain is kept in place by a catch mechanism, and released on demand by the user, for example between bites of food and between sips of liquid, by simultaneously pulling on the wire, string, or chain to release the head of face net.

Figure 3A:
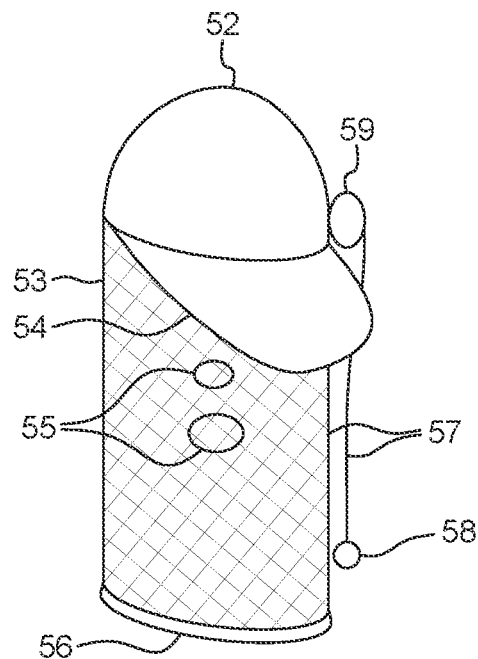
FIG. 3A illustrates one embodiment of a headgear with an article, such as a mesh or net, containing a photosensitizer formulation deployed from the headgear.
Figure 3B:
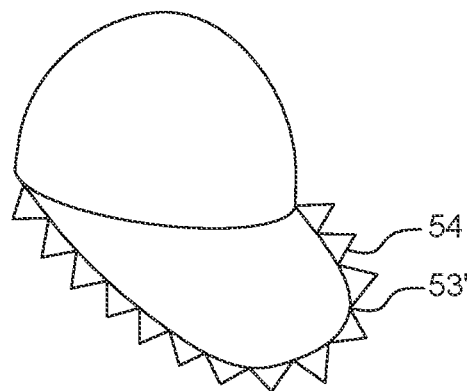
FIG. 3B illustrates the headgear of FIG. 3A with the article containing the photosensitizer formulation stored around the headgear.

FIG. 3A illustrates one embodiment of a hat 52 and a net 53 coated with a photosensitizer formulation. The net 53 hangs from the curvilinear edge of the hat brim 54 to provide a protective screen in front of the user's face and nose/mouth 55. In at least some embodiments, a curvilinear stiffening rod 56 is provided around the base of net 53. In at least some embodiments, an end of a drawstring 57 is attached to a bead 58 which aids in grasping the drawstring 57. The other end of the drawstring 57 is attached to the rod 56. When the user grasps the drawstring 57/bead 58 and pulls in a downward direction, the net 53 is raised by way of pulley wheel system 59 which is incorporated into the hat 52, for example, at the point where the lateral edge of the hat brim 54 joins the hat 52. This opens the net to expose the user's face. The retracted position of the net 53 just below the outer rim of the hat brim 54 is shown as the bunched net 53' in FIG. 3B.

In at least some embodiments, the net, netting, or mesh with a photosensitizer formulation applied thereto is supplied in packaging that is light-proof. In at least some embodiments, the net, netting, or mesh can be rolled-up, folded, compressed, or otherwise arranged in a smaller configuration. In at least some embodiments, the packaging is polymeric or metallic or any combination thereof. In at least some embodiments, the packaging is cylindrical. In at least some embodiments, the cylindrical packaging includes a dowel, bar, or tube, also cylindrical in shape, running along at least a portion of the length of the packaging. The net, netting, or mesh can be wound around the dowel, bar, or tube during storage. In at least some embodiments, an edge of the net, netting, or mesh can be grasped and pulled in one direction to rotate the net, netting, or mesh material on an axis around the dowel, bar, or tube deploying the net or mesh as a screen. In at least some embodiments, a photosensitizer formulation can be added to the packaging as needed when the screen is rolled back into the packaging using a hand crank or other device attached to the dowel, bar, or tube to enable continued antiviral activation when the net, netting, or mesh is re-deployed as a screen, after reapplication of the photosensitizer formulation in the packaging to the net, netting, or mesh.

In at least some embodiments, the net, netting, or mesh is packaged and stored in a folded state and can be deployed by unfolding. In at least some embodiments, after use, the net, netting, or mesh can be refolded and placed back in the packaging. In at least some embodiments, a photosensitizer formulation can be reapplied to the net, netting, or mesh when refolded or prior to redeployment.

In at least some embodiments, the net, netting, or mesh is attached to rods or struts (which may be supplied at different lengths) and can be folded or otherwise arranged as a pre-assembled product and optionally precoated with a photosensitizer formulation (or the photosensitizer formulation can be applied when the product is deployed.) The rods or struts are connected by hinges and can be deployed into a generally cuboid, rectangular cuboid, pyramid, sphere, or any other suitable regular or irregular shape.

In at least some embodiments, the product, when deployed, can form a free-standing structure. In at least some embodiments, the free-standing structure is a tent-like or cage-like structure and, at least in some embodiments, is capable of housing or isolating individuals or groups of individuals, animals, birds, or other living creatures. In this manner, transmission of virus or other pathogenic microbes can be prevented or reduced by way of photoactivation by light interaction with the photosensitizer formulation to produce singlet oxygen.

In at least some embodiments, the rods or struts are hollow and can be pre-filled with a photosensitizer formulation in a liquid solution. In at least some embodiments, the hollow rods or struts can incorporate pores, holes, or slits which allow the photosensitizer formulation to slowly flow onto the attached net, netting, mesh, or screen. In at least some embodiments, the net, netting, mesh, or screen can be configured to facilitate dispersal of the photosensitizer formulation by capillary action or wicking to renew the photosensitizer formulation on the net, netting, mesh, or screen from the rod or strut reservoir. In at least some embodiments, this arrangement can be used to maintain or renew photodynamic disinfection as the photosensitizer is photobleached.

In at least some embodiments, one or more of the rods or struts can incorporate at least one light source, such as a battery powered LED array. This light source can provide the activating light for the photosensitizer formulation or can augment the ambient light. In at least some embodiments, the net, netting, mesh, or screen is made at least partially of metal such as is used in common window screens. In at least some embodiments, the net, netting, mesh, or screen is made at least partially of a tear-resistant, polymeric material such as can be found in mosquito and bed netting. In at least some embodiments, the rods or struts or other supports for the net, netting, mesh, or screen includes nitinol wire or other shape memory materials.

In at least some embodiments, the net or mesh incorporates a hinged, folding frame (which may be lightweight) with a stand. In at least some embodiments, the frame stretches the net or mesh into a flat, two-dimensional configuration. Alternatively, in at least some embodiments, the frame can be opened such that it forms an angle. For example, the frame may allow the net, netting, screen, or mesh to assume a "V" shape.

Figure 3C:
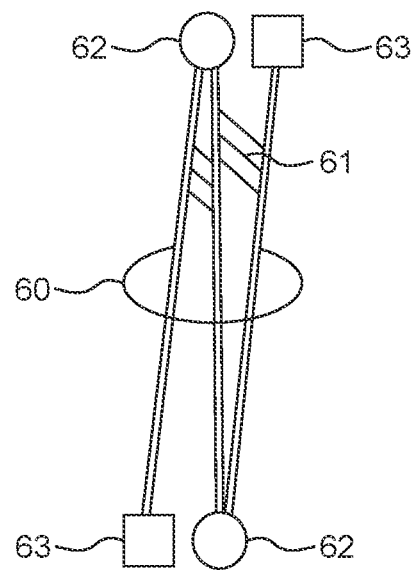
FIG. 3C illustrates one embodiment of an article having a set of rods or struts with at least one net containing a photosensitizer formulation attached thereto.
Figure 3D:
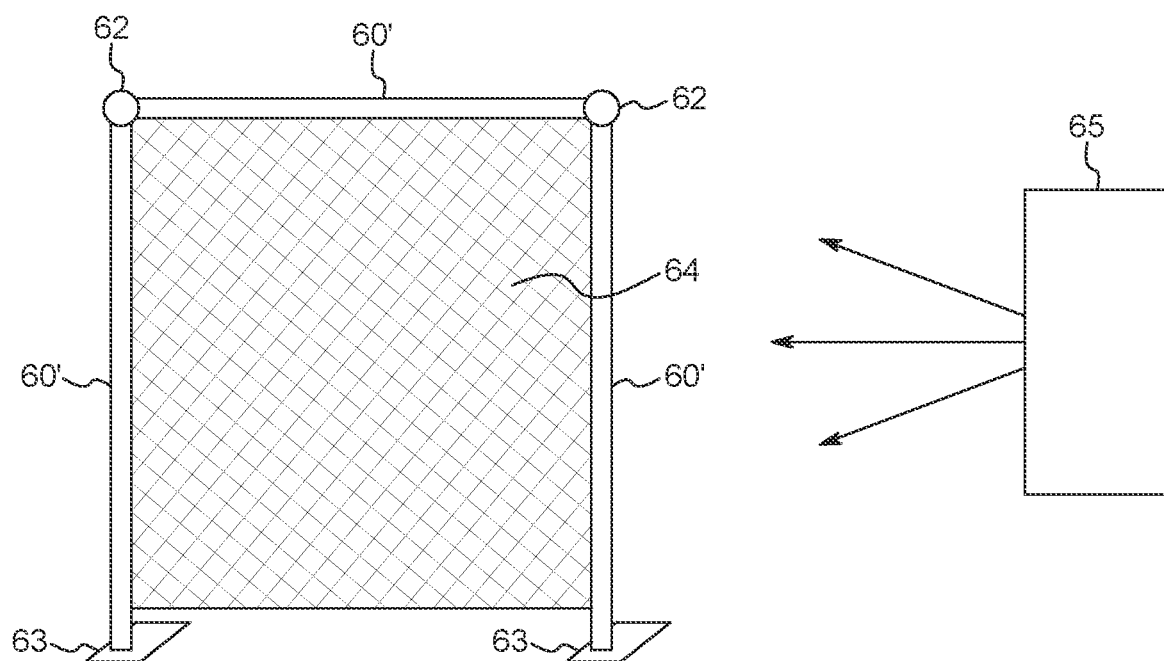
FIG. 3D illustrates the article of FIG. 3C deployed and illuminated by a light source.

FIG. 3C illustrates one embodiment of three rods 60 in a collapsed configuration. A net 61 (indicated by cross-hatching) is attached to the rods 60 along the edges of the rods. The net 61 is folded or bunched. A photosensitizer formulation coats the net 61. The rods 60 are joined by hinges 62 so that the rods 60 and net 61 can form a contiguous structure. Flat stands 63 are attached to the two distal ends of the contiguous structure formed by the rods 60. FIG. 3D illustrates the fully deployed net 64 attached to the deployed rods 60' which are moved into the position shown on the axis enabled by the hinges 62. The rods 60' are supported by the stands 63 and enable the deployed net 64, coated by the photosensitizer formulation, to act as an antimicrobial (e.g., antiviral) shield or barrier when illuminated by ambient light or by one or more light sources 65.

In at least some embodiments, a structure with the net, netting, mesh, or screen can provide an enclosure to house or isolate infected or potentially infected creatures such as, for example, farm animals or pets. In at least some embodiments, a structure can provide interconnected spaces with optional slits or openings such as loose or zipper bearing flaps, in the net, netting, mesh, or screen to allow for movement of creatures between the spaces if desired. Slits or openings in the net, netting, mesh, or screen may also allow a caretaker access to the interior of the structure for cleaning, feeding, caring, and monitoring the creatures. In at least some embodiments, tear resistant polymers or metals can be used for the net, netting, mesh, or screen to prevent or reduce rips and tears in the enclosure. Any suitable thickness or pattern of the net, netting, screen, or mesh can be used. In at least some embodiments, one or more light sources can be incorporated into the framework of the enclosures. In at least some embodiments, light sources may enhance photodisinfection at night or at low ambient light levels.

In at least some embodiments, the structure or enclosure can incorporate a polymeric or metallic floor. In at least some embodiments, the structure or enclosure can be stacked.

Figure 3E:
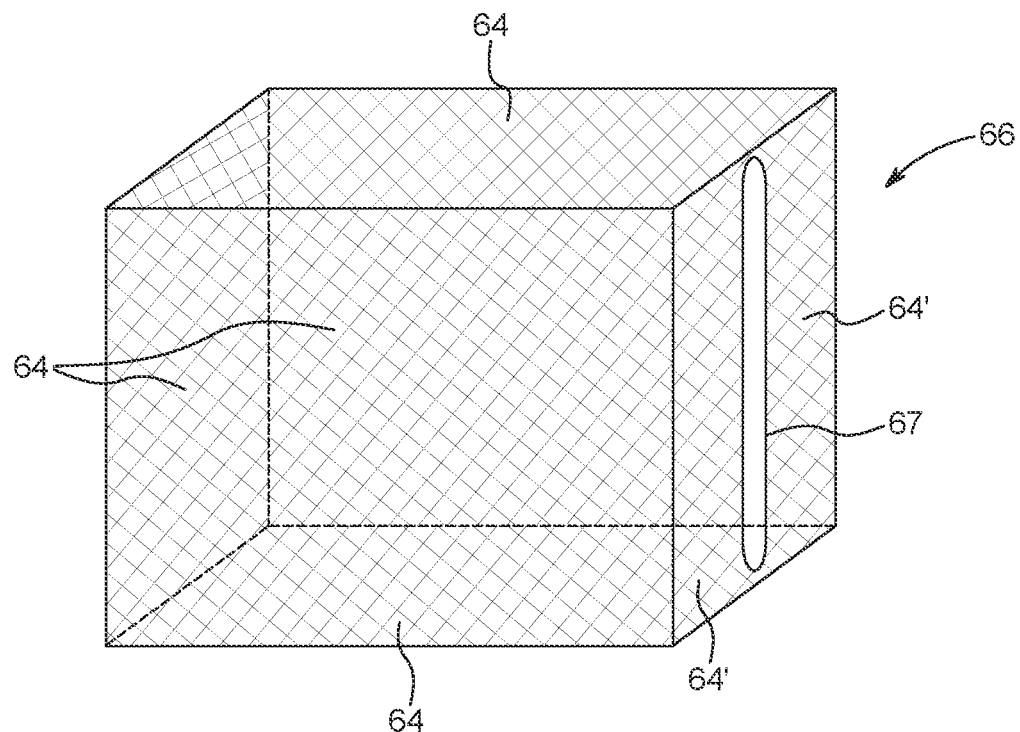
FIG. 3E illustrates one embodiment of a cage or container with a photosensitizer formulation deployed thereon.

FIG. 3E illustrates a four-walled, roofed animal house 66 that includes a metallic screen 64 that is coated with the photosensitizer formulation. The screen 64 form at least four walls and the roof of the animal house 66. In at least some embodiments, a flexible net 64' incorporating a slit 67 enables an animal caretaker to reach into the interior of animal house 66 as needed. The flexible net 64' can also be coated with the photosensitizer formulation.

Any of the nets, nettings, screens, or meshes described herein can incorporate polymeric strands, filaments, wicks, hollow perforated tubes, or elongate channels to provide for capillary action or wicking. When in contact with photosensitizer formulation, capillary action or wicking can provide for delivery of the photosensitizer formulation onto the net, netting, screen, or mesh to renew the photosensitizer formulation.

In at least some embodiments, the net, netting, screen, or mesh incorporates biodegradable material such as, for example, polylactic acid and derivatives thereof, silks, lactides, caprolactones, dioxanones, and glycolides.

In at least some embodiments, a film, net, netting, screen, or mesh can be made using cellulose and coated with the photosensitizer formulation. In at least some embodiment, the cellulose film, net, netting, screen, or mesh can be optically transparent.

In at least some embodiments, three-dimensional (3D) printing or any other suitable manufacturing method is used to make a clear polymer, microperforated screen that can be rigid or can be a flexible film. In at least some embodiments, a clear, flexible, microperforated film can be coated with the photosensitizer formulation and folded into a shape that can be contained in a jewelry pendant or locket to be worn by a user on a chain, string, or thick filament around the neck of the user. In at least some embodiments, the pendant or locket is hollow and hinged so that it can contain the film. The pendant or locket can be opened and the film deployed to produce singlet oxygen via the photosensitizer formulation. In at least some embodiments, the film is attached to the elongate jewelry pendant or locket so that when the pendant or locket is open, the film can hang vertically and be positioned around or over the user's nose and mouth. In at least some embodiments, as an example, the chain, string, or thick filament can be displaced from around the user's neck to a superior location such that it rests on the bridge of the user's nose and over the ears in the superior retroauricular location where the temple portion of the earpieces of a pair of glasses typically rests.

In at least some embodiments, a flexible, clear, microperforated film, coated with the photosensitizer formulation, can function as a mask. In at least some embodiments, the film can be rolled up on a neck chain, string, or thick filament and positioned on the posterior aspect of the user's neck. When the mask is desired, the film can be rotated to the anterior position of the neck to enable use by the user. In at least some embodiments, the neck chain, string, or thick filament segment with the attached film is draped on the bridge of the user's nose and around the ears, where the superior skin surface of the ear canal connects to the skin of the head. In at least some embodiments, a chin strap or fastener is provided as a component of the neck chain, string, or thick filament for use as a thin chin strap positioned under the user's chin to hold the film in place in front of the user's nose and mouth.

Figure 2A:
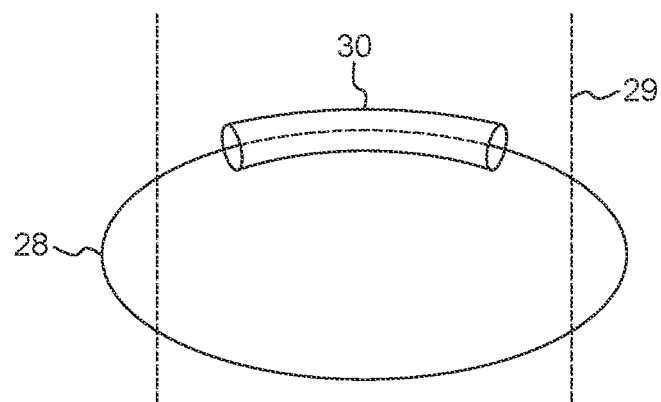
FIG. 2A illustrates one embodiment of a film with an applied photosensitizer formulation disposed on a chain around a user's neck.
Figure 2B:
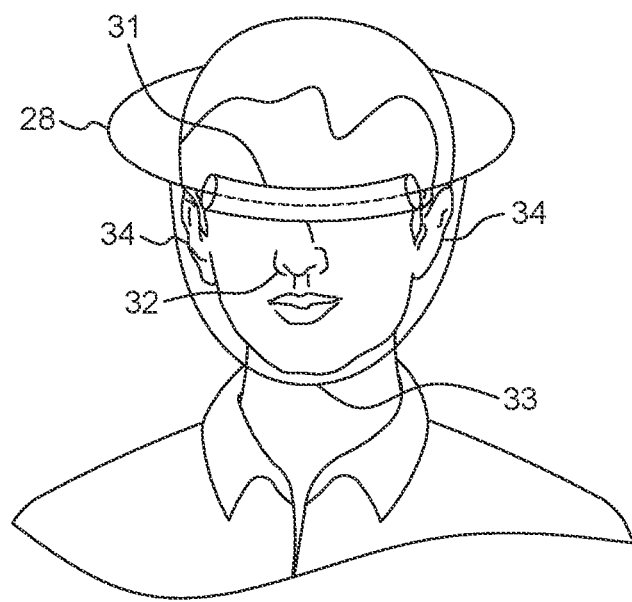
FIG. 2B illustrates positioning the film of FIG. 2A on the user ready for deployment.
Figure 2C:
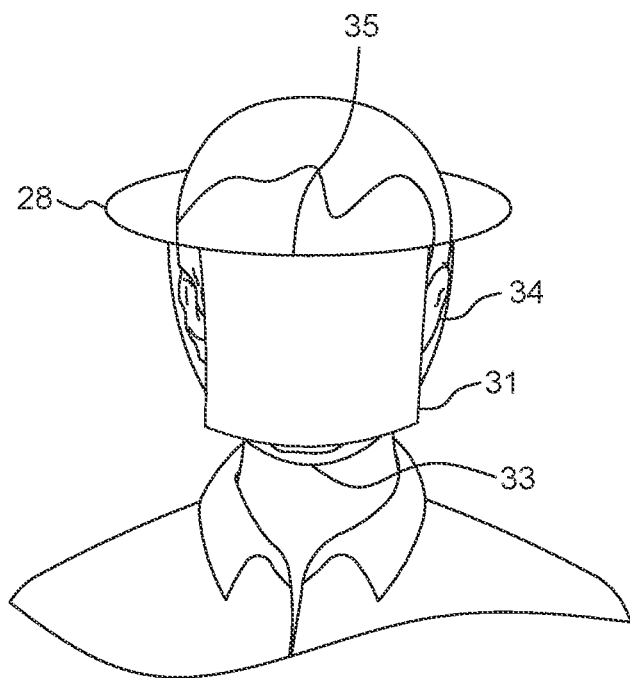
FIG. 2C illustrates deployment of the film of FIG. 2A.

FIG. 2A illustrates one embodiment of a neck chain, string, or thick filament 28 which is worn around the user's neck 29. A rolled up, clear, flexible, microperforated film 30, coated with the photosensitizer formulation, is disposed on the neck chain, string, or thick filament 28. When not in use, the film 30 can be positioned posterior to the neck. In FIG. 2B, the neck chain, string, or thick filament 28 is shown rotated and, in FIG. 2C, the film 31 is unrolled in front of the user's nose and mouth 32. In at least some embodiments, a chin strap 33 is attached to the neck chain, string, or thick filament 28. When in position, the film 31, coated with the photosensitizer formulation, can protect the user's nose and mouth 32 to provide a physical shielding effect through antimicrobial (e.g., antiviral) photoactivation via ambient light absorption by the photosensitizer formulation resulting in singlet oxygen generation. In at least some embodiments, the superior aspect of neck chain, string, or thick filament 28 is draped over the bridge of nose 35 and positioned over the ears 34 in a similar fashion to a pair of glasses enabling the film 31 to cover the nose and mouth 32.

In at least some embodiments, a transparent net can be easily and safely positioned around the head of an infected coughing patient. Patients afflicted with respiratory viral infections can cough droplets into the air harboring many millions of highly infectious viral particles which can travel many feet. These patients are typically cared for in isolation rooms with frequent air exchange to reduce airborne transmission risk. Despite this and other surface cleaning methods, healthcare workers caring for ill patients in these settings are at an elevated risk of contracting infections by viral inhalation or touching infected surfaces including the PPE they are using, equipment surfaces, and the patient. Patients who are sneezing and coughing are often not able to wear a close-fitting mask over the nose and mouth due to the unpleasant sensation of contamination and wetness due to sputum, saliva, and mucus expectorated or sneezed into the mask surface proximate to the patient's face.

In at least some embodiments, headwear with an attached net surrounds the patient's face and acts as a physical and an active anti-infective barrier due to the applied, light-activated photosensitizer formulation that is coated on the net and, optionally, the headwear. A patient who is coughing, sneezing, or exhaling pathogens into the air is treated in the prone position on a bed which aids in respiration. In at least some embodiments, a protective mesh or net with a coating of the photosensitizer formulation is positioned around the patient's head to reduce exposure of heath care workers and others in the patient's immediate environment and reduce contamination of the room and equipment and objects in the patient's room. In at least some embodiments, when the patient is in the prone position which improves respiration, the net surrounding the patient's face is braced in position using one or more thin rods or the like. In at least some embodiments, the thin rods can be positioned in a "U"-shaped orientation or a dome-shaped orientation to hold the netting away from the patient's face. In at least some embodiments, the distal ends of the "U"-shaped rods or dome-shaped rods are in contact with the patient's bed and the superior surface of the "U"-shaped or dome-shaped rods surrounds the patient's head and face.

In at least some embodiments, the net (for example, an electret net) contains a series of baffles on the side of the net the patient's face. The net surrounding the face and the baffles are coated with the photosensitizer formulation and also serve to enhance the capture of sputum, saliva, mucus, and respiratory droplets that would otherwise be ejected into the environment. The net/baffle head and face covering is preferably disposable because it will likely be contaminated.

In at least some embodiments, a net, netting, or mesh coated with the photosensitizer formulation, as well as the baffles, are made using an electret material that can aid in trapping airborne virus. In at least some embodiments, the net, netting, or mesh is optically transparent. The baffles are attached on at least one edge to the net, netting, or mesh with encompasses the patient's head and face to hold the baffles in place.

In at least some embodiments, a photosensitizer formulation is applied to a suit that includes a head and face protector contiguous with at least a neck and chest protector. In at least some embodiments, these protectors are made from a lightweight, flexible, breathable, optically transparent material. In at least some embodiments, the head, face, neck, arm, hand, and chest protector are fashioned into a transverse shape, shielding and protecting the anterior half of the body. In at least some embodiments, the material of these protectors is suspended from a frame allowing a user to step into the protective garment with the user's arms extended, hands extended into gloves, and the user's face and head simultaneously moving into a position inside of the head and face and neck protector. In at least some embodiments, the material of the neck and chest protector, as well as the gloves, is impermeable to fluids. The head protector optionally includes a mesh or net attached to a hat that is designed to keep the mesh or net from contacting the user's skin.

In at least some embodiments, an optically transparent face shield is incorporated into a head protector and bonded to a net. The face shield can protect the face from fluid splashes and airborne contamination. The lateral aspects of the headwear include a mesh or net coated with the photosensitizer formulation to facilitate respiration by the user and limit facial sweat.

In at least some embodiments, the suit is kept in a folded configuration in a light-proof package or container which can be rapidly opened in an emergency. In at least some embodiments, the suit is folded in such a way so that the head protector is exposed first, grasped first, and pulled over the user's head by the user. Then the arms are inserted into the sleeves, and the hands into the gloves. Then the chest protector is secured using, for example, a simple clasp, or a magnetic closure, posteriorly.

During a medical emergency involving a patient who is infected or may possibly be infected with a transmissible virus, or dangerous microorganism, in at least some embodiments, a physician, nurse, or other healthcare worker can open a lightproof cabinet or a lightproof bag containing any of the suits described above. In at least some embodiments, the donning sequence for the suit can be taught or training sessions conducted to enable emergency effective use of this rapid donning suit.

In at least some embodiments, a net, netting, or mesh (which may be transparent or rigid or both) is incorporated into a helmet, such as a head-protective sports helmet, with the net, netting, or mesh positioned and affixed in front of the user's face. In at least some embodiments, the net or mesh is attached to the rim of the helmet or to a protective grille which may be part of the helmet protecting the face. In at least some embodiments, the net, netting, or mesh is attached and held in a stretched, fully deployed arrangement to prevent direct contact with the user's face. The net, netting, or mesh is coated with the photosensitizer formulation to facilitate disinfection of air proximate to the user's mouth and nose prior to inhalation. The net, netting, or mesh may also disinfect the user's exhaled air as it passes through the net, netting, or mesh.

In at least some embodiments, a sport participant's face and head is protected by a helmet or a hat that includes a shield over the face. In at least some embodiments, the shield is flexible or semi-flexible and can be optically clear. The shield can be coated with the photosensitizer formulation. In at least some embodiments, the shield accommodates and enables deep and rapid breathing. In at least some embodiments, the shield incorporates a system of baffles which are coated with the photosensitizer formulation. The incorporation of baffles increases the surface area which can trap and disinfect airborne pathogens, microbials, and viruses.

In at least some embodiments, a military style protective helmet (or other helmet, such as a motorcycle helmet or bicycle helmet) includes a net, netting, or mesh that is coated with a photosensitizer formulation. In at least some embodiments, the net, netting, or mesh is suspended from the forehead rim portion of the helmet. In at least some embodiments, the net, netting, or mesh is attached to the helmet rim lateral to the face on both sides of the helmet to protect the side of the face. In at least some embodiments, the net, netting, or mesh can be camouflage-colored or printed with a camouflage pattern.

In at least some embodiments, the helmet, net, netting, or mesh can incorporate at least one LED, an LED array, or any other suitable light source. For example, a light source can be affixed to the anterior aspect of the helmet above eye level. In at least some embodiments, the light source is powered by a battery (which may be rechargeable) or by a solar panel incorporated into the helmet. In at least some embodiments, the battery can be incorporated in the helmet.

In at least some embodiments, the helmet can include at least one optical fiber coupled to the light source. In at least some embodiments, each optical fiber can run the length of the net, netting, or mesh vertically or horizontally or in any other direction or combination of directions. In at least some embodiments, a network of optical fibers to distribute light across the mesh, netting, or net can facilitate a very low light level that photoactivates the photosensitizer formulation and may also reduce unwanted detectability in low light level conditions. In at least some embodiments, indocyanine green (ICG) is used as a photosensitizer in the photosensitizer formulation to the net, netting, or mesh. Illumination of ICG with dim near infrared light may reduce risk of detection of the light when used in dark environments.

The net, netting, or mesh can be flexible or stiff. In at least some embodiments, the net, netting, or mesh is arranged on the helmet so that it is positioned away from the face (for example, by at least one centimeter.)

Figure 2D:
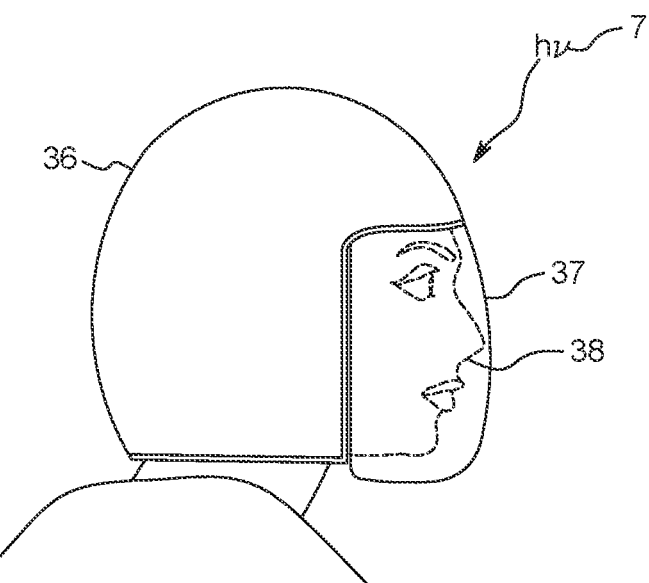
FIG. 2D illustrates one embodiment of a helmet with a face covering having an applied photosensitizer formulation.

FIG. 2D illustrates a helmet 36 incorporating a net or mesh 37 coated with a photosensitizer formulation. The net or mesh 37 provides microbiocidal protection in ambient or applied light 7.

In at least some embodiments, optically clear fibers, strands, or monofilaments can be oriented vertically (or in any other direction(s)) and coated with the photosensitizer formulation. In at least some embodiments, the fibers, strands, or monofilaments hang in a vertical orientation in front of the user's face when the user is in an upright position. In at least some embodiments, the fibers, strands, or monofilaments can be separated manually by the user enabling the user to eat and drink by reaching through the vertically oriented fibers, strands, or monofilaments. In at least some embodiments, the curtain of fibers, strands, or monofilaments hangs from an elastic band or strap which wraps around a hat or around the head of the user. The fibers, strands, or monofilaments are coated with the photosensitizer formulation to disinfect air around the user and reduce infection by airborne viruses or other microbes.

In at least some embodiments, the fibers, strands, or monofilaments are draped from a flexible chain, string, wire, or cable that fits arounds the user's ears and bridge of the user's nose. This arrangement can provide a scaffold from which the strands, fibers, or monofilaments are suspended and can, in at least some embodiments, appear as a vertically oriented screen-like curtain. The strands, fibers, or monofilaments are coated with a photosensitizer formulation which when exposed to light creates a microbiocidal (e.g., virucidal) singlet oxygen barrier in front of the user's nose and mouth. In at least some embodiments, when the user is eating or drinking, a mechanical pulley system is coupled to the strands, fibers, or monofilaments to retract the strands, fibers, or monofilaments in two directions laterally, exposing the user's mouth so that food or liquid can be directed into the user's mouth. In at least some embodiments, the pulley system is automated such that a sensor detects the user's hand and arm motion towards the user's mouth and retracts the curtain.

In at least some embodiments, a small magnetic clasp enables quick and convenient change of position of the vertically hanging strands, fibers, or monofilaments into a bunched or clustered position. When the magnetic clasp is disengaged, the strands, fibers, or monofilaments, can resume the vertical protective position in front of the user's mouth and nose.

Figure 2E:
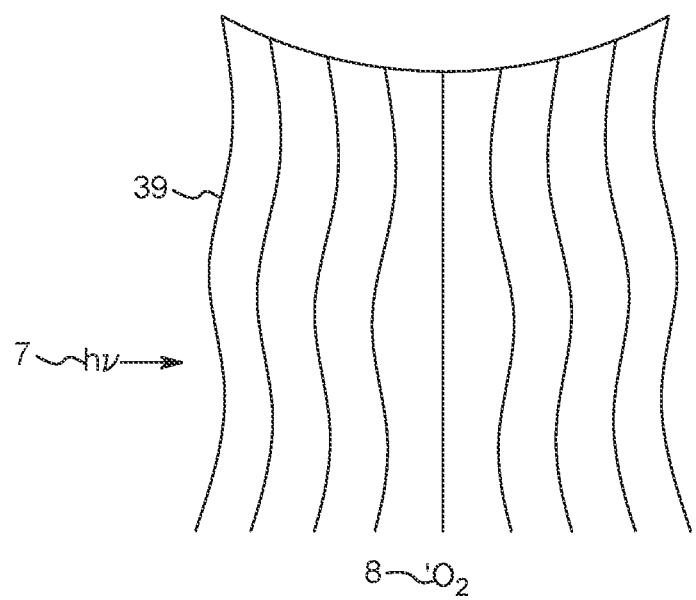
FIG. 2E illustrates one embodiment of a curtain of strands, fibers, or monofilaments having an applied photosensitizer formulation.
Figure 2F:
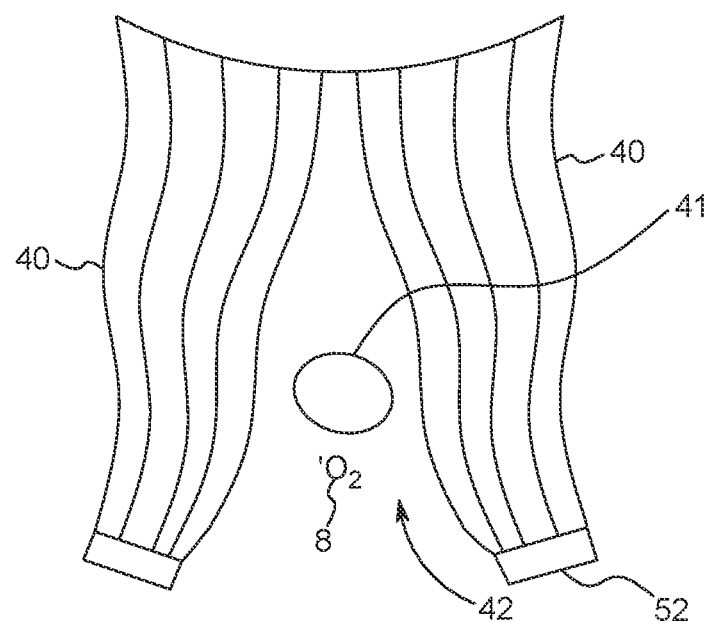
FIG. 2F illustrates the curtain of FIG. 2E with some strands, fibers, or monofilaments drawn apart using a clasp.

FIGS. 2E and 2F illustrate fibers, strands, or monofilaments 39 hanging in a vertical orientation in front of the user's face when the user is in an upright position. The fibers, strands, or monofilaments 39 are coated with a photosensitizer formulation that is photoactivated by ambient or other light 7 to produce microbicidal (e.g., virucidal) singlet oxygen 8. In FIG. 2F, the fibers, strands, or monofilaments are shown drawn away together as indicated by position 40 to permit access to the user's mouth 41 through the gap 42. Magnetic clasp 52 is shown drawing fibers, strands, or monofilaments 40 together.

In at least some embodiments, a person at an eating establishment dons a transparent head net coated with a photosensitizer formulation which incorporates a small magnet located at the bottom of net, and a second magnet incorporated into the head net at a level which is approximately one inch (about 2.5 centimeters) above the level of the mouth. The user uses one hand to raise the bottom of the head net above the mouth level, and engages the two magnets, which creates a space for delivery of food and drink by the other had to the user's mouth. The magnets are disengaged after food or drink are in the mouth, re-establishing full face protection.

In at least some embodiments, the vertically oriented fibers, strands, or monofilaments coated with a photosensitizer formulation are incorporated into a bed net which encloses an infected patient. In at least some embodiments, the fibers, strands, or monofilaments form a curtain positioned proximate to the patient's face so that a caregiver is able to reach through the curtain to feed the patient, administer oral medications, measure the patient's temperature, or the like. In at least some embodiments, the user has a curtain of fibers, strands, or monofilaments as described above and sits within a netting or mesh. The fibers, strands, or monofilaments, as well as the netting or mesh, are coated by a photosensitizer formulation.

In at least some embodiments, a transparent head net incorporates at least one small magnet which is attached to a thin, stiff rod along the bottom edge of the net. A second magnet of opposite polarity is incorporated into the head net at a distance of between 1-3 centimeters, above the level of the upper lip, laterally, or in the midline with respect to the mouth. The bottom magnet at the free edge of the head net is located in the midline of the rod, or at the lateral edge of the rod on the right or the left side of the user. If the user is right-handed, the left hand is used to vertically lift the magnet and brings the lower magnet of opposite polarity up to meet the upper magnet which engage magnetically. Thus, a space is created through which the user can pass his/her hand, holding a fork or spoon for example, into his/her mouth. In a similar fashion, the user can sip liquids from a glass or cup or from a straw. In at least some embodiments, during the act of chewing or swallowing, the magnetic clasp is disengaged by the same hand used to engage the magnets and lower the head net back to the fully protective position. In this way, the nose and eyes of the user remain protected at all times by the head net while eating or drinking.

In at least some embodiments, a facemask allows fluids to be imbibed without removal of the facemask. The facemask incorporates a polymeric tube similar to a drinking straw that transgresses the face mask material at one lateral edge of the mask. In at least some embodiments, two polymeric tubes similar to drinking straws penetrate a face mask, with one tube near one lateral edge, and the other located at the opposite side, near the other lateral edge. In at least some embodiments, the tube is flexible and penetrates the face mask material such that the outer wall of the tube is flush with the face mask material and sealed at the penetration point. In at least some embodiments, the distal end of the tube is closed with an air- and fluid-tight polymeric membrane to prevent or reduce entry of aerosols or airborne infected droplets. The membrane can be pierced by a separate drinking straw with a beveled tip. In at least some embodiments, the inner diameter of the tube ranges from two millimeters to five millimeters and the length of the tube external to the face mask ranges from 1 centimeter to 6 centimeters in length. In at least some embodiments, at the tube penetration point into the face mask, the inner tube length ranges from 3 to 6 centimeters in length. In at least some embodiments, the inner tube is attached or fixed to the inner mask surface, with the exception of the proximal tip which makes a 45 to 90-degree bend, with the proximal extension not in contact with the inner mask surface having a length of 1 to 3 centimeters.

In at least some embodiments, the proximal opening of the tube is proximate to the user's lips but isn't in contact with the user's lips. However, the user is able to extend his/her lips to surround the proximal opening of the inner polymeric tube, which is open, and thus able to imbibe liquids while wearing the face mask. In at least some embodiments, liquids are delivered through a separate straw that pierces the distal membrane of the external segment of the tube. In at least some embodiments, the external segment of the tube lies flat against the outer surface of the face mask, extending in a lateral direction, away from the center point of the face mask. In at least some embodiments, each opening of the tube can be crimped, the outer distal end of the tube manually, and the inner proximal opening crimped by pressure exerted by the user's lips. Crimping both ends of the tube obviates risk of airborne aerosol or droplet transmission into the interior volume of the mask.

In at least some embodiments, the tube incorporates filtration material as is used for water filtration in products such as LifeStraw® as an added barrier, preventing accidental microbial ingestion. The distal end of the polymeric tube can also be sealed using a biocompatible pressure sensitive adhesives coating and/or by incorporating a high surface energy plastic at the distal tip, and optionally at the proximal tip to aid in creating a seal after imbibing liquid with pressure applied to the tube ends.

Figure 3F:
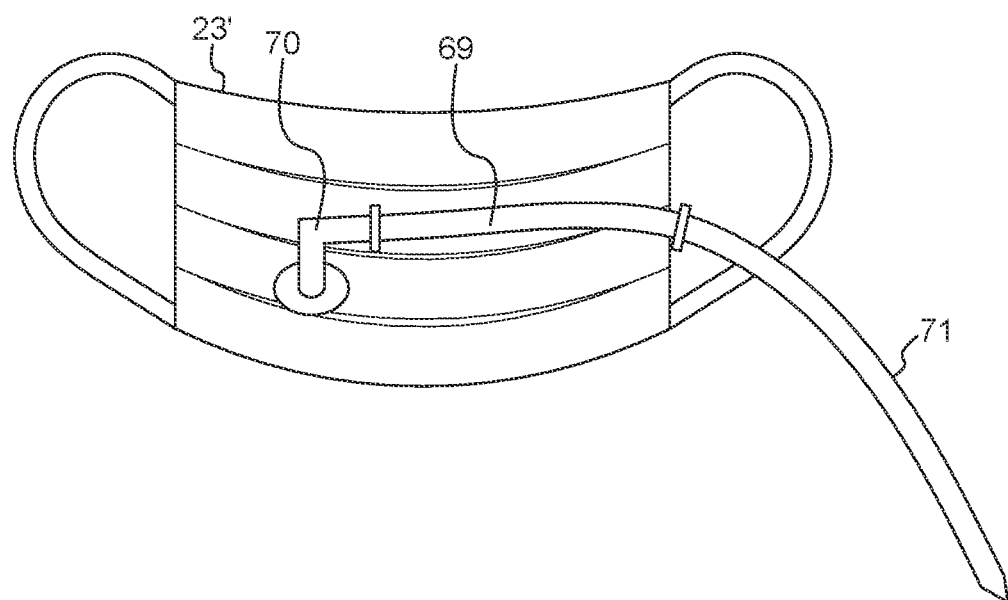
FIG. 3F illustrates one embodiment of a face mask with a tube attached thereto for intake of fluids by a user.

FIG. 3F illustrates one embodiment of a face mask 23' with straps 68 for positioning the mask. A flexible polymeric tube 69 is affixed to the inner surface of face mask 23' and has a right-angle bend 70 to enable the user wearing the face mask 23' to engage the tube 69 with his/her lips for purposes of imbibing liquids. In at least some embodiments, liquids are delivered by way of a beveled straw 71 which extends to a liquid container. The beveled straw 71 is inserted into the mouth of polymeric tube 69' which is located on the outer surface of face mask 23'.

In at least some embodiments, applicators can be used to dispense and evenly apply the photosensitizer formulation to a surface to be disinfected or to provide a disinfection-active surface. In at least some embodiments, the handle of the applicator is made of a flexible, compressible polymer that is configured as a hollow cylinder. The cylindrical handle is grasped in one hand and, when gently squeezed forces, an amount of the photosensitizer formulation out of the distal end of the applicator. In at least some embodiments, the amount of photosensitizer formulation delivered to the distal end of the applicator is proportionate to the compressive force generated by the squeezing action. In at least some embodiments, the distal end of the applicator is a sponge or a squeegee. In at least some embodiments, the photosensitizer formulation is delivered to the distal end of the flexible polymeric squeegee by way of a series of hollow channels incorporated into the substance of the squeegee blade. The hollow channels can be oriented in parallel or in a fan shape and terminate in an opening at the distal end of the squeegee blade for delivery of the photosensitizer formulation to a surface.

In at least some embodiments, a childproof cap protector covers the distal sponge applicator. In at least some embodiments, the cap prevents unwanted spillage or dispensing of the photosensitizer formulation, as well as protecting against accidental ingestion.

Singlet oxygen can react with proteins, lipids, and other viral and microbial constituents over relatively short distances. To disinfect airborne viruses at a longer distance, the molecular ground state oxygen can travel at a relatively high velocity so that singlet oxygen generated from a light activated photosensitizer formulation can travel a larger distance (for example, up to 15 cm.) In at least some embodiments, at least one ultrasound transducer proximate to the photosensitizer formulation can be used to propel the singlet oxygen molecules. In at least some embodiments, air is propelled by a high-speed fan over a photosensitizer formulation which is stationary or confined and exposed to light. As air is passed at relatively high velocity over the photosensitizer formulation, the light activated photosensitizer formulation generates singlet oxygen which is then propelled by the fan. In at least some embodiments, a magnetic field is used to accelerate air over a photosensitizer formulation which is stationary or confined and exposed to light.

In at least some embodiments, a photosensitizer formulation is contained within a hollow, malleable tube. In at least some embodiments, the tube can be conformed while maintaining its lumen and does not crimp when bent. In at least some embodiments, the tube outer diameter ranges from 1.5 to 10 mm. In at least some embodiments, the tube contains multiple perforations (for example, perforations that are no more than 1.0 mm in diameter and spaced apart by 0.1 to 1.0 mm). In at least some embodiments, the tube can be placed in proximity to a user's face and provide a singlet oxygen cloud in the path of expected airflow upon user inspiration. In at least some embodiments, the tube is made of a transparent, gas-permeable, polymer that allows ambient light to photoactivate the photosensitizer formulation in order to generate singlet oxygen from ground state molecular oxygen. In at least some embodiments, the tube is, or can be, connected to a blower to distribute the singlet oxygen over a greater distance due to air egress from the tube perforations.

Figure 2G:
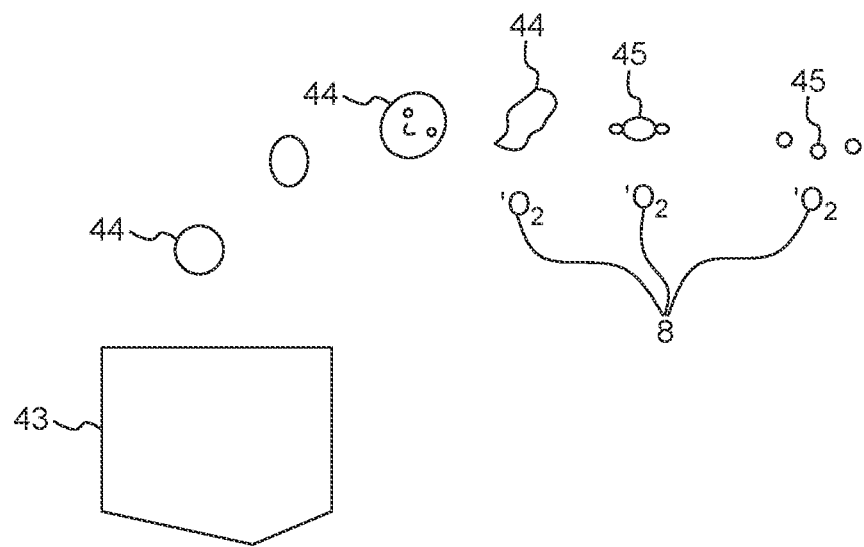
FIG. 2G illustrates one embodiment of a bubbler generating bubbles with incorporated singlet oxygen generated by a photosensitizer formulation in the bubbler.

In at least some embodiments, surfactants or emulsifiers can be used to form bubbles containing singlet oxygen. In at least some embodiments, bubbles incorporating singlet oxygen are produced by passing air through a gas-permeable membrane incorporating a photosensitizer formulation that is exposed to photoactivating light (for example, ambient light or light from a LED or other light source). The photosensitizer formulation diffuses into, or otherwise combines with, the surfactant or emulsion as the surfactant or emulsion formulation is agitated to form bubbles. The agitation process can create thin-walled bubbles which degrade, or "pop" releasing the singlet oxygen into the ambient atmosphere to produce virucidal or antimicrobial action. FIG. 2G illustrates a bubble maker 43 (e.g., a bubbler) emitting bubbles 44 containing singlet oxygen 8 which is released into the ambient air as the bubble 45 degrades.

In at least some embodiments, the bubbles containing singlet oxygen are ejected or dispersed into air by a fan or a blower during the agitation process. In at least some embodiments, the fan or blower and the bubble-maker are positioned in front of the user. In at least some embodiments, a singlet oxygen bubbler with a dispersal mechanism can disinfect air, as well as surfaces in contact with the air including surfaces that are otherwise difficult to access.

In at least some embodiments, a device incorporates at least one light source capable of activating a photosensitizer formulation applied or embedded in a filter membrane. In at least some embodiments, the photosensitizer formulation is illuminated by the light source and the resulting singlet oxygen diffuses into a surfactant or emulsifier solution. This solution can be formed into bubbles. For example, one or more blades are wet in the surfactant or emulsion solution and then positioned in front of the air flow of a fan or blower to create bubbles. Another example is a bubble ring that rotates into a surfactant or emulsion solution and then rotates in front of a fan or blower to eject bubbles into the air. When the bubble wall degrades, singlet oxygen is released to encounter pathogenic microbes or viruses in the air.

In at least some embodiments, an air stream is generated by a fan or a blower which forces air through a transparent tube that contains, or has an inner surface coated with, the photosensitizer formulation. The transparent tube is illuminated by ambient light or a light source, such as an LED light array, which photoactivates the photosensitizer formulation to generate a singlet oxygen stream. In at least some embodiments, the air stream generated by the fan or blower is dehumidified by forcing the air stream though a dehumidifying agent or desiccant, such as, for example, silica, calcium chloride, powdered charcoal, or the like or any combination thereof. Dehumidifying the air may reduce the quenching of singlet oxygen from singlet oxygen collisions with airborne water molecules and may increase singlet oxygen travel and volume of distribution.

Figure 4A:
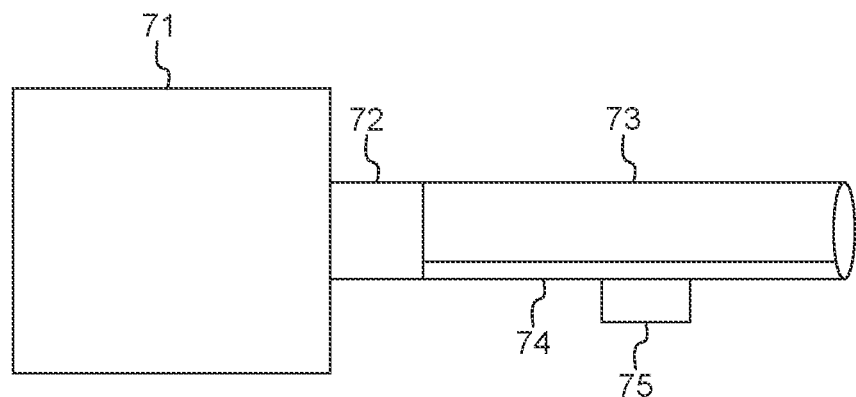
FIG. 4A illustrates one embodiment of a blower, a desiccant layer, and a tube with a photosensitizer formulation deployed therein.
Figure 4B:
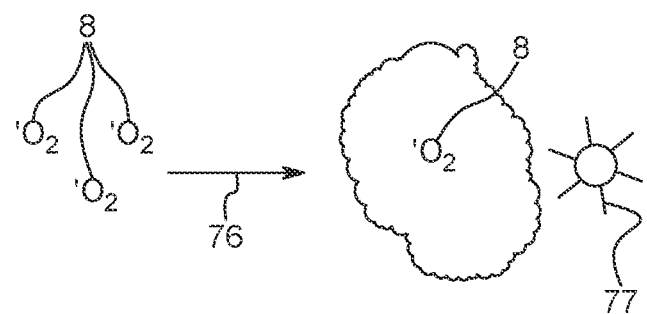
FIG. 4B illustrates photoactivation of a photosensitizer formulation to generate singlet oxygen from ambient molecular oxygen.

FIG. 4A illustrates a blower 71 which generates an air stream passing through a desiccant layer 72. An air permeable tube 73 is attached to the blower 71 and contains a photosensitizer formulation 74 within the tube or on the tube's inner surface. Air dehumidified by the desiccant 72 is forced through the tube 73 where singlet oxygen molecules 8 are generated by photoactivation of the photosensitizer formulation 74 by ambient light or a light source, such as an LED 75. As illustrated in FIG. 4B, singlet oxygen molecules 8 in the form of a cloud are propelled from the mouth of polymeric tube 73 into the ambient air as indicated by the directional arrow 76. A singlet oxygen molecule cloud 8' binds with virus particles 77 (or other microbes) to inactivate the airborne virus particles 77.

In at least some embodiments, a battery-powered drone hovers above a user's head to shower the user's face with virucidal and microbicidal singlet oxygen. The drone includes a photosensitizer formulation supplied from a reservoir in the drone and dispersed onto a rotating fan which also serves as the hovering mechanism for the drone. The photosensitizer formulation is photoactivated by ambient light or a light source to generate singlet oxygen.

Figure 5A:
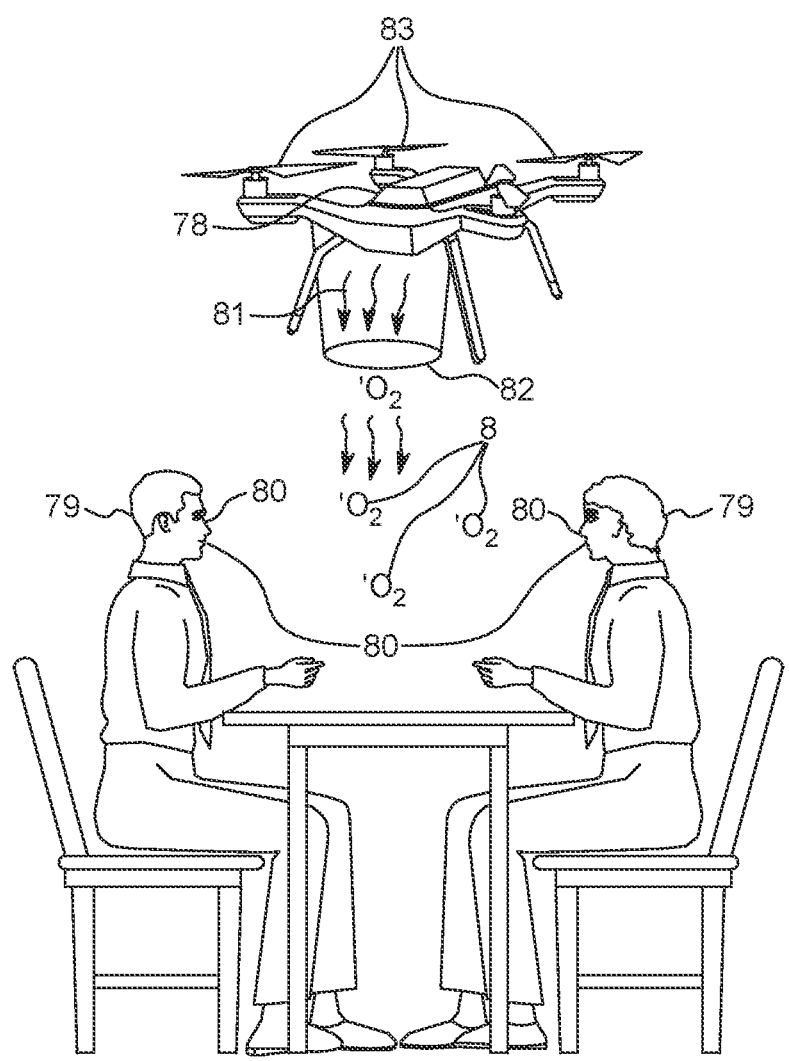
FIG. 5A illustrates one embodiment of an airborne device, such as a drone, for spreading singlet oxygen using a photosensitizer formulation.

FIG. 5A illustrates a battery powered drone 78 hovering above users' heads 79. The drone 78 can shower the users' faces and the space 80 between them with virucidal and microbicidal singlet oxygen 8 generated by a light source 81 (or ambient light) which photoactivates a photosensitizer formulation supplied from an incorporated reservoir 82 onto the rotating fan 83 which also serves as the hovering mechanism for the drone.

Figure 5B:
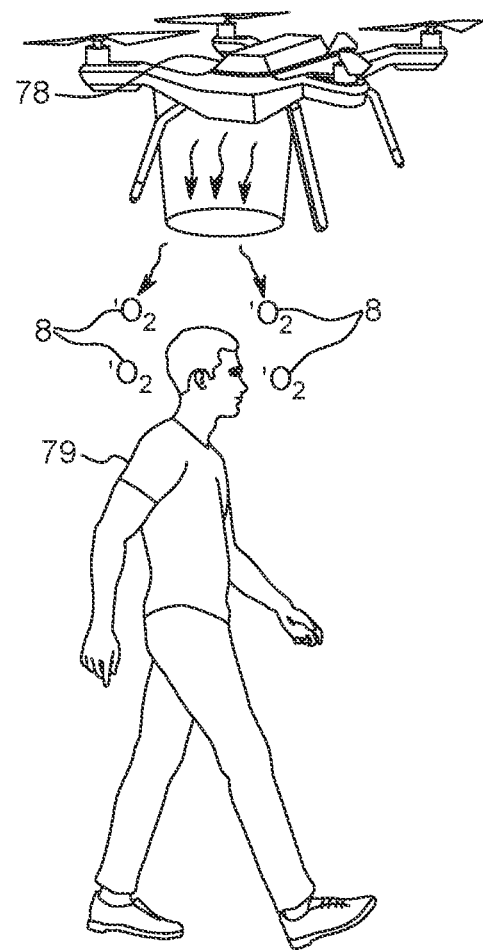
FIG. 5B illustrates another embodiment of an airborne device, such as a drone, for spreading singlet oxygen using a photosensitizer formulation.

In at least some embodiments, a drone is used to shower a user with singlet oxygen bubbles (using, for example, the bubbler described above). In at least some embodiments, any of the drones described herein are programmed to track follow the user's movements to provide antimicrobial disinfection even when the user is mobile. FIG. 5B illustrates a drone 78 that showers a user 79 with singlet oxygen 8 and is programmed to track the user's movements to provide antimicrobial disinfection even when the user is mobile.

Methylene blue and other photosensitizers also fluoresce. A fluorescence detector can include a light source that emits light within the absorption spectra of the photosensitizer formulation and a detector for detecting the fluorescence. In at last some embodiments, the detector can communicate physically or wirelessly to a smartphone or tablet or laptop to provide the fluorescence measurement. In at least some embodiments, the measurement can be used to guide reapplication of the photosensitizer formulation as singlet oxygen generation drops due to photobleaching or to detect counterfeit photosensitizer formulations with no or incorrect photoactive composition. Any suitable light source can be used (such as a LED which may be powered by a battery). In at least some embodiments, a lens is provided to focus the emitted light on a region of interest.

As an example, in at least some embodiments, an excitation light source (for example, a laser diode emitting at 665 nm) can be combined with a 688 nm emission detector (to detect fluorescence of methylene blue in response to the excitation) to ascertain when methylene blue photobleaching has occurred due to low emission signal. In at least some embodiments, the light source is a red LED with an overlying filter which limits the emitted light to 665-666 nm, and the detector is tuned to capture the 688 nm fluorescence emission with an optional filter enabling only the emitted fluorescence of methylene blue to be detected by the detector.

In at least some embodiments, the excitation and detection devices are housed in a small enclosure. In at least some embodiments, this enclosure can be attached to a smartphone incorporating an app/software enabling a readout of the emitted light. In at least some embodiments, the emission and detection wavelengths are selected for detection of another photosensitizer that fluoresces. In at least some embodiments, a decrease of the fluorescent signal can indicate photobleaching and the need for application of the photosensitizer formulation.

Figure 2H:
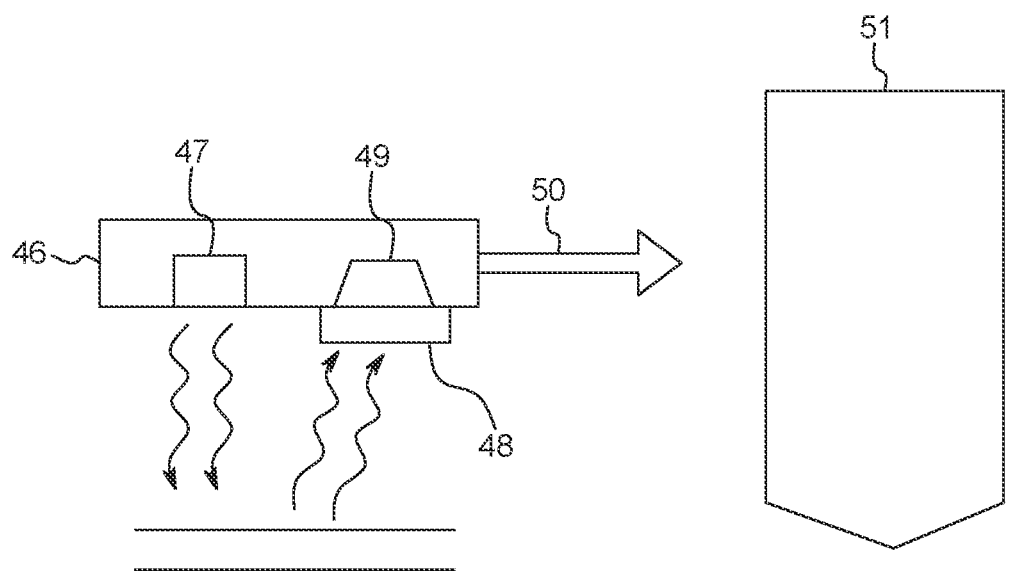
FIG. 2H illustrates one embodiment of a fluorescent detection device.

FIG. 2H illustrates a fluorescence detection device 46 that includes at least one LED emitter 47 (or other light source) and at least one detector 48. In at least some embodiments, the fluorescence detection device 46 also includes a signal processor and transmitter 49 which transmits a signal 50 to a smartphone 51 or other device where the signal is interpreted by the user for determination of photosensitizer formulation activity or photobleaching.

In at least some embodiments, an article includes a substrate; a photosensitizer formulation disposed on or in the substrate; and a fluorescent formulation coupled to, disposed on, or disposed in the substrate, wherein fluorescence of the fluorescent formulation is indicative of photobleaching of the photosensitizer formulation. In at least some embodiments, the substrate is a piece of personal protective equipment. In at least some embodiments, the substrate is a mesh, net, netting, screen, or curtain of strands, fibers, or monofilaments. In at least some embodiments, the fluorescent formulation includes fluorescein. In at least some embodiments, the fluorescent formulation is disposed on a strip or film attached to the substrate. In at least some embodiments, the article further includes a light source configured to induce fluorescence of the fluorescent formulation. In at least some embodiments, the article further includes a detector configured to receive and measure the fluorescence of the fluorescent formulation. In at least some embodiments, the article further includes a device (for example, a smart phone, cell phone, tablet, or laptop with an application) configured to receive the measurement of the fluorescence from the detector and provide an indication of the fluorescence or the photobleaching to a user based on the measurement.

In at least some embodiments, the device can also be used to detect counterfeit or imitation products not using a photosensitive formulation. For example, a counterfeit product may incorporate a non-photoactive blue dye and be detectable as counterfeit due to the lack of a fluorescent signal or an incorrect fluorescent signal.

In at least some embodiments, a photosensitizer that is also a visible fluorophore, such as, for example, indocyanine green (ICG) or fluorescein or a combination thereof, can be applied to a net, netting, mesh, mask, PPE, or other material or to a surface to be disinfected. In at least some embodiments, this formulation can be applied to a flat disc (or other shape) of material with a sticky backing protected by a peel away protector for ease of initial and repeat application of the disc. Decrease in the fluorescence signal can be used to determine photobleaching of the photosensitizer formulation and the need for reapplication of the photosensitizer formulation.

Fluorescein can be excited by a blue light source, such as a single blue light emitting LED, or a white light source and will emit a visible green, fluorescent light. ICG can be excited by a near infrared light emitting LED around 800 nm. In at least some embodiments, a blue film light filter, such as a piece of blue colored cellophane or plastic film, is placed over a white light source, such as a LED incorporated into a smartphone or a small flashlight and used to induce visible greenish fluorescence from a fluorescein impregnated indicator. The degradation of the fluorescence visible to the naked eye is used as a surrogate indicator of photobleaching of the photosensitizer formulation and the need for replenishment of the photosensitizer formulation.

In at least some embodiments, one or more photosensitizers (such as methylene blue) are combined with a fluorophore (such as fluorescein) as an indicator. The rate of decreased fluorescence can be correlated to the rate of photobleaching of the photosensitizer formulation.

In at least some embodiments, a dry fluorescein formulation (for example, a formulation having a fluorescein concentration ranging from 0.1% to 0.0000001%) is applied to a paper strip, a film, a disc, or other object with a sticky backing. The paper strip, film, disc, or other object is applied to the surface of an object, such as PPE, with a coating of the photosensitizer formulation. A drop of water placed on the surface of the paper strip or other film enables visualization of fluorescently emitted light which is green to yellow green in ambient light. The photobleaching rate of the fluorescein can be related to the photobleaching rate of the photosensitizer formulation in that light and provides a visible indicator of the photobleaching of the photosensitizer formulation. When the visible emission of the fluorescein fades, the user can re-apply the photosensitizer formulation. In at least some embodiments, the fluorescein indicator is intermittently excited by a light source and the presence or absence of emitted fluorescent light acts a guide to the need for reapplication of the photosensitizer formulation.

In at least some embodiments, a light meter is incorporated into a smart phone, smart device, or other device to measure the ambient light fluence rate and spectrum. In at least some embodiments, these readings can be used to estimate singlet oxygen generation from a photosensitizer formulation that is coated or applied to a face mask, to a head net, a screen or mesh, or a surface such as a user's skin or an inanimate surface to be disinfected. In at least some embodiments, the smart phone, smart device, or other device incorporates an app which integrates known rates of singlet oxygen generation from a photosensitizer formulation coating in different light conditions and the photobleaching rate. In at least some embodiments, in variable lighting conditions, for a given photosensitizer formulation concentration and volume, a predicted rate of singlet oxygen production can be calculated by the app programming and displayed for the user.

In at least some embodiments, a selection of personal protective equipment is supplied as a kit that also contains a photosensitizer formulation dispenser with a quantity of photosensitizer formulation. In at least some embodiments, the dispenser is contained in a child-proof container or a pouch or bag. The personal protective equipment in the kit can include any or all of the following: protective garments, head coverings (for example, a hat or helmet with an attached net or mesh), gloves (for example, nitrile gloves), face coverings (for example, eye protecting goggles or glasses, a mask, or other face covering), a bed net or other net (which may be washable or reusable), or the like or any combination thereof.

For example, for a nursing home, or for an infected person quarantining at home or being treated in a medical setting, a kit may include a bed net (which may be washable and reusable), a transparent screen (for use as an active antiviral shield between the patient and caregivers), a photosensitizer formulation, an applicator, and a light source. For schools or other sites, a kit could include at least one head net (sized for a child in the case of a school kit), a photosensitizer formulation, one or more adjustable screens which are free standing, and a riboflavin/hyaluronic acid disinfectant formulation for skin and surface (which may be provided in the form of wipes or in a dispenser.) As another example, a hospital visitor (or other individual) may be issued a kit containing a head net, a facemask, a gown, and gloves (or the like or any combination thereof), all of which are coated with the photosensitizer formulation. Such a kit may facilitate safer visitation by reducing risk of transmission by the visitor, if infected, to others or by reducing risk of visitor infection by patients.

In at least some embodiments, a kit can include one or more nets, nettings, meshes, or screens with applied photosensitizer formulation along with a support structure, such as rods or struts. The kit can be used to isolate infected patients or animals to reduce possible infection of other individuals or animals. In at least some embodiments, the kit contains head netting with applied photosensitizer formulation. The kit may also include additional photosensitizer formulation, an applicator, and, optionally, a fluorescence detection arrangement that enables a user to ascertain when photobleaching occurs. In at least some embodiments, the rods, struts, or head nets optionally incorporate at least one LED, an array of LEDs, or any other suitable light source for photoactivating the photosensitizer formulation. In at least some embodiments, the kit can be accessed for deployment on demand to prevent viral and other pathogenic microbial transmission.

In at least some embodiments, nets, nettings, meshes, or screens can be placed around non-living creatures or inanimate objects which may harbor, or be contaminated with, pathogens. In at least some embodiments, this arrangement may reduce or prevent aerosolization into the ambient environment of pathogens exposed to moving air or liquid solutions. In at least some embodiments, potentially infectious microorganisms can be inactivated or destroyed on the surface, or proximate to the surface, of the nets, nettings, meshes, or screens.

In at least some embodiments, a child-proof container or pouch can be used as a receptacle for the application of the photosensitizer formulation to a mask, face covering, net, netting, or mesh enabling effective dispersal of the photosensitizer formulation onto the material surface and preventing or reducing spillage or unwanted aerosolization of the photosensitizer into the ambient environment if administered as a spray. In at least some embodiments, a child-proof container or pouch is sized to accommodate a face mask, a net or mesh head covering, or a folded screen or net and incorporates an inlet which conforms to the mouth of a device or container with the photosensitizer formulation. The mouth of the device or container is the outlet through which the photosensitizer formulation is delivered.

In at least some embodiments, if an outbreak occurs, deep cleaning of floors, walls, ceilings, equipment, tools, and other objects in the environment can be accomplished using photosensitizer formulations. In at least some embodiments, the photosensitizer formulation is non-toxic or edible so that cleaning can occur without evacuation of inhabitants which could be required if using bleach, for example.

In at least some embodiments, antigen detection and immune cell reactivity can be assayed using saliva or analyzing the breath of the user. For example, the assay may utilize functionalized graphene sensors which can be incorporated into the fabric of a mask or face covering. FIG. 6B illustrates one embodiment of mask 87 with a functionalized graphene sensor. In FIG. 6C, a mask 88 has been exposed to breath activating the sensor.

In at least some embodiments, a fabric or mesh can be selected which can incorporate photochromic reactive molecules that admit a certain intensity range of light under most ambient light conditions encountered. Limiting the intensity of light using the photochromic technology can facilitate the photosensitizer activation process.

In at least some embodiments, the coloration of the fabric, net, or mesh incorporating a photosensitizer formulation reflects the spectrum of light most likely to be absorbed by the photosensitizer formulation.

Chitosan is a nontoxic, biodegradable biopolymer derived by deacetylation of chitin from a variety of sources including, but not limited to, shrimp, crab, lobster shells, and mushrooms. In at least some embodiments, chitosan, or any suitable chitosan derivative, is combined with at least one photosensitizer to form a photosensitizer formulation. Although any chitosan can be used, in at least some embodiments, the chitosan has low molecular weight 50,000-190,000 Da, medium molecular weight 190,000-310,000 Da, or high molecular weight 310,000-375,000 Da. In at least some embodiments, the photosensitizer is selected from methylene blue, riboflavin, erythrosine, rose bengal, indocyanine green, curcumin, bergamot, or any combination thereof. In at least some embodiments, the photosensitizer can be combined with chitosan, or any suitable chitosan derivative, using any suitable technique including, but not limited to, application of cold plasma, acidic chemical agents (such as, but not limited to, lactic acid, citric acid, acetic acid, or hydrochloric acid), basic chemical agents (such as sodium hydroxide), heat, photochemical bonding, bioprinting, or any other additive process.

In at least some embodiments, chitosan, or any suitable chitosan derivative, may take the form of a gel, film, fiber, scaffold, bead, hydrogel, particles, powder, tablet, granules, sponge, or the like or can be incorporated into a textile or other material. In at least some embodiments, the chitosan, or any suitable chitosan derivative, results in textile or material that are breathable and hydrophobic. The combination of chitosan, or any suitable chitosan derivative, and photosensitizer can provide for surface disinfection and immunogen generation when used in light. Because chitosan is a charged substance (with the ability to capture viruses and other pathogens), lightweight, breathable, and hydrophobic, splash-resistant fabrics can be made. These fabrics may replace traditional impermeable, stiff, uncomfortable, and heat-retaining personal protective garments. In at least some embodiments, chitosan, or any suitable chitosan derivative, and one or more photosensitizers can be combined in liquid formulations for use as a disinfectant spray.

In at least some embodiments, use data for antimicrobial products (for example, masks, garments, headwear, nets, meshes, gloves, or the like incorporating a photosensitizer formulation) is captured through a questionnaire filled out by the user or other designated person to document the use of the antimicrobial products. Information may include, but is not limited to, time of use, location of use, demographic data, anonymized personal health data, personal contacts, and related data regarding local microbial transmission rates. In at least some embodiments, the questionnaire can be incorporated into an app downloaded to a smartphone, tablet, or other convenient computing device for ease of use. In at least some embodiments, the questionnaire can also ask if and when the user becomes symptomatic from an infectious agent of interest.

In at least some embodiments, the data can be captured and transmitted for analysis at a central location to ascertain product usage and effectiveness in reducing infection rates in a particular setting or location. For example, in a nursing home located in an area where an outbreak of a pathogenic microorganism has occurred, use of protective PPE and other products incorporating a photosensitizer formulation can be compared to a different nursing home also in the area with a comparable patient population and staffing. Data on usage and infection rates can be used for product development, improvement, and for business purposes. In at least some embodiments, physiological data obtained from wearables, such as smart watches, or from medical records can also be captured and analyzed to ascertain not only infection rates, but severity of infections and sequelae of infections, comparing use and non-use of the antimicrobial products. In at least some embodiments, use of active antimicrobial PPE with applied photosensitizer formulation can be compared to use of ordinary conventional PPE, as an example, to ascertain infection reduction rate on a personal level, compare severity of infections, and to compare overall infection rates in the at-risk populations.

In at least some embodiments, a sensor can be incorporated into the packaging or container containing the antimicrobial product. The sensor detects when the package is opened and the product deployed. In at least some embodiments, a radiofrequency identification (RFID) tag or chip can be incorporated into the package or container. In at least some embodiments, the packaging or container can include a QR code or barcode. In at least some embodiments, when the antimicrobial product is to be used, the RFID tag or chip, QR code, or barcode is scanned using a handheld scanner or reader commonly utilized in medical settings to document and track usage of medical equipment and drugs. The use of the antimicrobial products such as antiviral PPE or antiviral nets, meshes, or shields having the light-activated photosensitizer formulation, is documented. In at least some embodiments, the use timing and patterns are communicated to a central source using the RFID scanner or reader or by the personnel responsible for deploying the antimicrobial product. At the central source, the data is integrated and analyzed statistically to determine efficacy of the antimicrobial products and to improve the products.

What is claimed as new and desired to be protected is:

1. An article, comprising:
    a substrate that is arranged as a mask or a face covering; and
    a photosensitizer formulation disposed on or in the substrate with a concentration gradient of a photosensitizer formation along at least one dimension of the substrate, wherein the photosensitizer formulation, when in contact with molecular oxygen and activated by light or ultrasound, produces microbicidal singlet oxygen configured to damage at least one microbe and generate antigenic particles.

2. The article of claim 1, wherein the substrate is a net, netting, or mesh.

3. The article of claim 1, wherein the substrate is a curtain of strands, fibers, or monofilaments.

4. The article of claim 1, further comprising a light source incorporated in, or coupled to, the substrate.

5. A kit, comprising:
    the article of claim 4; and a
    a pair of glasses that incorporates the light source.

6. A kit, comprising:
    the article of claim 1; and
    a saliva assay to assess a user response to the antigenic particles.

* * * * *